(12) United States Patent
Kitano

(10) Patent No.: US 12,042,322 B2
(45) Date of Patent: Jul. 23, 2024

(54) PROCESSING APPARATUS, METHOD OF OPERATING PROCESSING APPARATUS, AND OPERATION PROGRAM FOR PROCESSING APPARATUS

(71) Applicant: FUJIFILM CORPORATION, Tokyo (JP)

(72) Inventor: Koichi Kitano, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 504 days.

(21) Appl. No.: 17/335,078

(22) Filed: Jun. 1, 2021

(65) Prior Publication Data

US 2021/0378617 A1 Dec. 9, 2021

(30) Foreign Application Priority Data

Jun. 5, 2020 (JP) .................................. 2020-098878

(51) Int. Cl.
*A61B 6/00* (2024.01)
*G01S 17/894* (2020.01)
(Continued)

(52) U.S. Cl.
CPC ............ *A61B 6/5258* (2013.01); *A61B 6/544* (2013.01); *G01S 17/894* (2020.01); *G06T 5/70* (2024.01); *G06T 5/73* (2024.01); *A61B 6/025* (2013.01)

(58) Field of Classification Search
CPC ....... A61B 6/5258; A61B 6/544; A61B 6/025; G01S 17/894; G06T 5/002; G06T 5/003
See application file for complete search history.

(56) References Cited

U.S. PATENT DOCUMENTS 5,854,710 A * 12/1998 Rao .......................... G02B 5/23
430/21
2006/0210134 A1* 9/2006 Grass ..................... A61B 6/504
382/130
(Continued)

FOREIGN PATENT DOCUMENTS

JP 2004-209152 A 7/2004
JP 2010-057573 A 3/2010
(Continued)

OTHER PUBLICATIONS

English language translation of the following: Office action dated Mar. 22, 2023 from the JPO in a Japanese patent application No. 2020-098878 corresponding to the instant patent application. This office action translation is submitted now in order to supplement the understanding of the cited references which are being disclosed in the instant Information Disclosure Statement.

*Primary Examiner* — David P Porta
*Assistant Examiner* — Mamadou Faye
(74) *Attorney, Agent, or Firm* — SOLARIS Intellectual Property Group, PLLC

(57) ABSTRACT

A body thickness conversion unit converts a body thickness from a distance image imaged by a distance measurement camera to acquire the body thickness. A strength setting unit sets strength of noise reduction processing to a radiographic image to be stronger as the body thickness is thicker. A radiographic image acquisition unit acquires the radiographic image output from a radiation detector in radioscopy. A noise reduction processing unit executes the noise reduction processing on the radiographic image with the strength set by the strength setting unit.

12 Claims, 26 Drawing Sheets

(51) Int. Cl.
*G06T 5/70* (2024.01)
*G06T 5/73* (2024.01)
*A61B 6/02* (2006.01)

(56) References Cited

U.S. PATENT DOCUMENTS

| | | | |
|---|---|---|---|
| 2010/0142792 A1* | 6/2010 | Sakaguchi | G06T 5/002 |
| | | | 382/128 |
| 2016/0019701 A1 | 1/2016 | Visser et al. | |
| 2016/0354052 A1* | 12/2016 | Kawanishi | A61B 6/5282 |
| 2017/0065244 A1* | 3/2017 | Taki | A61B 6/544 |
| 2020/0237332 A1* | 7/2020 | Wang | A61B 6/5241 |
| 2021/0161501 A1 | 6/2021 | Sendai | |
| 2021/0342978 A1* | 11/2021 | Yu | G06T 5/002 |

FOREIGN PATENT DOCUMENTS

| | | |
|---|---|---|
| JP | 2015-167613 A | 9/2015 |
| JP | 2016-022095 A | 2/2016 |
| JP | 2017-051395 A | 3/2017 |
| JP | 2019-202087 A | 11/2019 |
| JP | 2020-099538 A | 7/2020 |
| WO | 2010/097941 A1 | 9/2010 |
| WO | 2020/036225 A1 | 2/2020 |

* cited by examiner

<GAUSSIAN FILTER PROCESSING>

FIG. 17

| STRENGTH TABLE (RECURSIVE FILTER PROCESSING) —103R | | |
|---|---|---|
| BODY THICKNESS | NUMBER OF IMAGES TO BE ADDED | WEIGHTING COEFFICIENT |
| < 10 cm | 3 | K1 = 1, K2 = 0.5, K3 = 0.25 |
| ≥ 10 cm AND < 15 cm | 5 | K1 = 1, K2 = 0.8, K3 = 0.6, K4 = 0.4, K5 = 0.2 |
| ≥ 15 cm AND < 20 cm | 7 | K1 = 1, K2 = 0.85, K3 = 0.7, K4 = 0.55, K5 = 0.4, K6 = 0.25, K7 = 0.1 |
| ... | | |

THICK →

STRONG →

FIG. 18

| STRENGTH TABLE (MEDIAN FILTER PROCESSING) | —103M |
|---|---|
| BODY THICKNESS | SIZE |
| < 10 cm | 3×3 |
| ≥ 10 cm AND < 15 cm | 5×5 |
| ≥ 15 cm AND < 20 cm | 7×7 |
| ⋮ | |

THICK ↓  STRONG ↓

FIG. 19

STRENGTH TABLE (GAUSSIAN FILTER PROCESSING) — 103G

| BODY THICKNESS | SIZE 3×3 | 5×5 | 7×7 |
|---|---|---|---|
| < 10 cm | | | |
| ≥ 10 cm AND < 15 cm | | | |
| ≥ 15 cm AND < 20 cm | | | |
| ... | | | |

THICK → / STRONG →

5×5 (X=256) — 110

| 1/X | 4/X | 6/X | 4/X | 1/X |
|---|---|---|---|---|
| 4/X | 16/X | 24/X | 16/X | 4/X |
| 6/X | 24/X | 36/X | 24/X | 6/X |
| 4/X | 16/X | 24/X | 16/X | 4/X |
| 1/X | 4/X | 6/X | 4/X | 1/X |

7×7 (X=4096) — 110

| 1/X | 6/X | 15/X | 20/X | 15/X | 6/X | 1/X |
|---|---|---|---|---|---|---|
| 6/X | 36/X | 90/X | 120/X | 90/X | 36/X | 6/X |
| 15/X | 90/X | 225/X | 300/X | 225/X | 90/X | 15/X |
| 20/X | 120/X | 300/X | 400/X | 300/X | 120/X | 20/X |
| 15/X | 90/X | 225/X | 300/X | 225/X | 90/X | 15/X |
| 6/X | 36/X | 90/X | 120/X | 90/X | 36/X | 6/X |
| 1/X | 6/X | 15/X | 20/X | 15/X | 6/X | 1/X |

FIG. 22A

| BODY THICKNESS | EDGE ENHANCEMENT PROCESSING |
|---|---|
| < 10 cm | NOT EXECUTE |
| ≥ 10 cm AND < 15 cm | NOT EXECUTE |
| ≥ 15 cm AND < 20 cm | EXECUTE |
| ⋮ | |

— 125A

↓ THICK  ↓ STRONG

FIG. 22B

| BODY THICKNESS | EDGE ENHANCEMENT PROCESSING |
|---|---|
| < 10 cm | LEVEL 1 |
| ≥ 10 cm AND < 15 cm | LEVEL 2 |
| ≥ 15 cm AND < 20 cm | LEVEL 3 |
| ⋮ | |

— 125B

↓ THICK  ↓ STRONG

LEVEL 1 < LEVEL 2 < LEVEL 3 < ⋯

PROCESSING APPARATUS, METHOD OF OPERATING PROCESSING APPARATUS, AND OPERATION PROGRAM FOR PROCESSING APPARATUS

CROSS-REFERENCE TO RELATED APPLICATIONS

The present application claims priority under 35 U.S.C. § 119 to Japanese Patent Application No. 2020-098878, filed on Jun. 5, 2020. The above application is hereby expressly incorporated by reference, in its entirety, into the present application.

BACKGROUND

1. Technical Field

A technique of the present disclosure relates to a processing apparatus, a method of operating a processing apparatus, and an operation program for a processing apparatus.

2. Description of the Related Art

In a medical field, for example, a radioscopy apparatus is used for various operations, such as a gastric barium test, cystography, and orthopedic reduction. The radioscopy apparatus continuously irradiates a subject with radiation in a comparatively low dose from a radiation source and displays radiographic images output from the radiation detector on a display in a form of video in real time.

In the radioscopy apparatus, as described above, the comparative low dose is set to suppress exposure of the subject. For this reason, the dose of the radiation that is transmitted through the subject and reaches the radiation detector is slight, and noise of the radiographic image is conspicuous. Accordingly, in the related art, for example, as described in JP2019-202087A, noise reduction (hereinafter, abbreviated as NR) processing is executed on the radiographic images. In JP2019-202087A, as the NR processing, recursive filter processing of adding, to a radiographic image to be processed, a radiographic image output further in the past than the radiographic image to be processed is exemplified. Spatial filter processing using a spatial filter, such as a median filter or a Gaussian filter, is also exemplified.

SUMMARY

The dose of the radiation that is transmitted through the subject and reaches the radiation detector depends on a body thickness of the subject. Noise of the radiographic image also depends on the body thickness of the subject. That is, in a case where the body thickness of the subject is thick, the dose of the radiation that reaches the radiation detector is extremely smaller, and noise of the radiographic image is more conspicuous. Accordingly, appropriate NR processing corresponding to the body thickness of the subject is needed. However, JP2019-202087A does not describe execution of appropriate NR processing corresponding to the body thickness of the subject.

An object of the technique of the present disclosure is to provide a processing apparatus, a method of operating a processing apparatus, and an operation program for a processing apparatus capable of executing appropriate noise reduction processing corresponding to a body thickness of a subject.

To achieve the above-described object, the present disclosure provides a processing apparatus that is used for a radioscopy apparatus including a radiation source configured to continuously irradiate a subject with radiation and a radiation detector configured to detect the radiation transmitted through the subject to output a radiographic image. The processing apparatus comprises at least one processor. The processor is configured to acquire a body thickness of the subject measured by a body thickness measurement sensor, set strength of noise reduction processing to the radiographic image to be stronger as the body thickness is thicker, acquire the radiographic image output from the radiation detector, and execute the noise reduction processing on the radiographic image with the set strength.

It is preferable that the processor is configured to execute, as the noise reduction processing, recursive filter processing of adding a past image as the radiographic image output further in the past than a processing target image as the radiographic image to be processed to the processing target image.

It is preferable that the processor is configured to set at least one of the number of past images added to the processing target image or a weighting coefficient to the past image to set the strength.

It is preferable that the processor is configured to execute, as the noise reduction processing, spatial filter processing using a spatial filter.

It is preferable that the processor is configured to set at least one of a coefficient or a size of the spatial filter to set the strength.

It is preferable that the processor is configured to execute edge enhancement processing of enhancing an edge of a structure in which a spatial frequency is relatively low in the radiographic image.

It is preferable that the processor is configured to set a tube current for performing the irradiation of the radiation to be lower as the body thickness is thicker, and make the radiation source perform the irradiation of the radiation with the set tube current.

It is preferable that the processor is configured to make the body thickness measurement sensor measure the body thickness in a case where the irradiation of the radiation is not performed.

It is preferable that the processor is configured to make the body thickness measurement sensor measure the body thickness in synchronization with a timing at which the radiation detector outputs the radiographic image for offset correction.

It is preferable that the body thickness measurement sensor is a distance measurement camera that outputs a distance image representing a distance to a surface of an object using a time-of-flight system, and the processor is configured to convert the body thickness from the distance image.

The present disclosure provides a method of operating a processing apparatus that is used for a radioscopy apparatus including a radiation source configured to continuously irradiate a subject with radiation and a radiation detector configured to detect the radiation transmitted through the subject to output a radiographic image. A processor executes body thickness acquisition processing of acquiring a body thickness of the subject measured by a body thickness measurement sensor, strength setting processing of setting strength of noise reduction processing to the radiographic image to be stronger as the body thickness is thicker, image acquisition processing of acquiring the radiographic image output from the radiation detector, and image processing of executing the noise reduction processing on the radiographic image with the set strength.

The present disclosure provides an operation program for a processing apparatus that is used for a radioscopy apparatus including a radiation source configured to continuously irradiate a subject with radiation and a radiation detector configured to detect the radiation transmitted through the subject to output a radiographic image. The operation program causes a processor to execute body thickness acquisition processing of acquiring a body thickness of the subject measured by a body thickness measurement sensor, strength setting processing of setting strength of noise reduction processing to the radiographic image to be stronger as the body thickness is thicker, image acquisition processing of acquiring the radiographic image output from the radiation detector, and image processing of executing the noise reduction processing on the radiographic image with the set strength.

According to the technique of the present disclosure, it is possible to provide a processing apparatus, a method of operating a processing apparatus, and an operation program for a processing apparatus capable of executing appropriate noise reduction processing corresponding to a body thickness of a subject.

BRIEF DESCRIPTION OF THE DRAWINGS

Exemplary embodiments according to the technique of the present disclosure will be described in detail based on the following figures, wherein:

FIG. 3A shows a manner in which the radiation generation unit is directed toward the left, and FIG. 3B shows a manner in which the radiation generation unit is directed toward the right;

FIG. 17 is a diagram showing a strength table for recursive filter processing;

FIG. 18 is a diagram showing a strength table for median filter processing;

FIG. 19 is a diagram showing a strength table for Gaussian filter processing;

FIGS. 22A and 22B are tables showing strength of edge enhancement processing depending on the body thickness, FIG. 22A shows an example where setting is made such that the edge enhancement processing is not executed in a case where the body thickness is less than a threshold value and the edge enhancement processing is executed in a case where the body thickness is equal to or greater than the threshold value, and FIG. 22B shows an example where setting is made such that a level of strength of the edge enhancement processing is made to be higher as the body thickness is thicker;

DETAILED DESCRIPTION

First Embodiment

Figure 1:
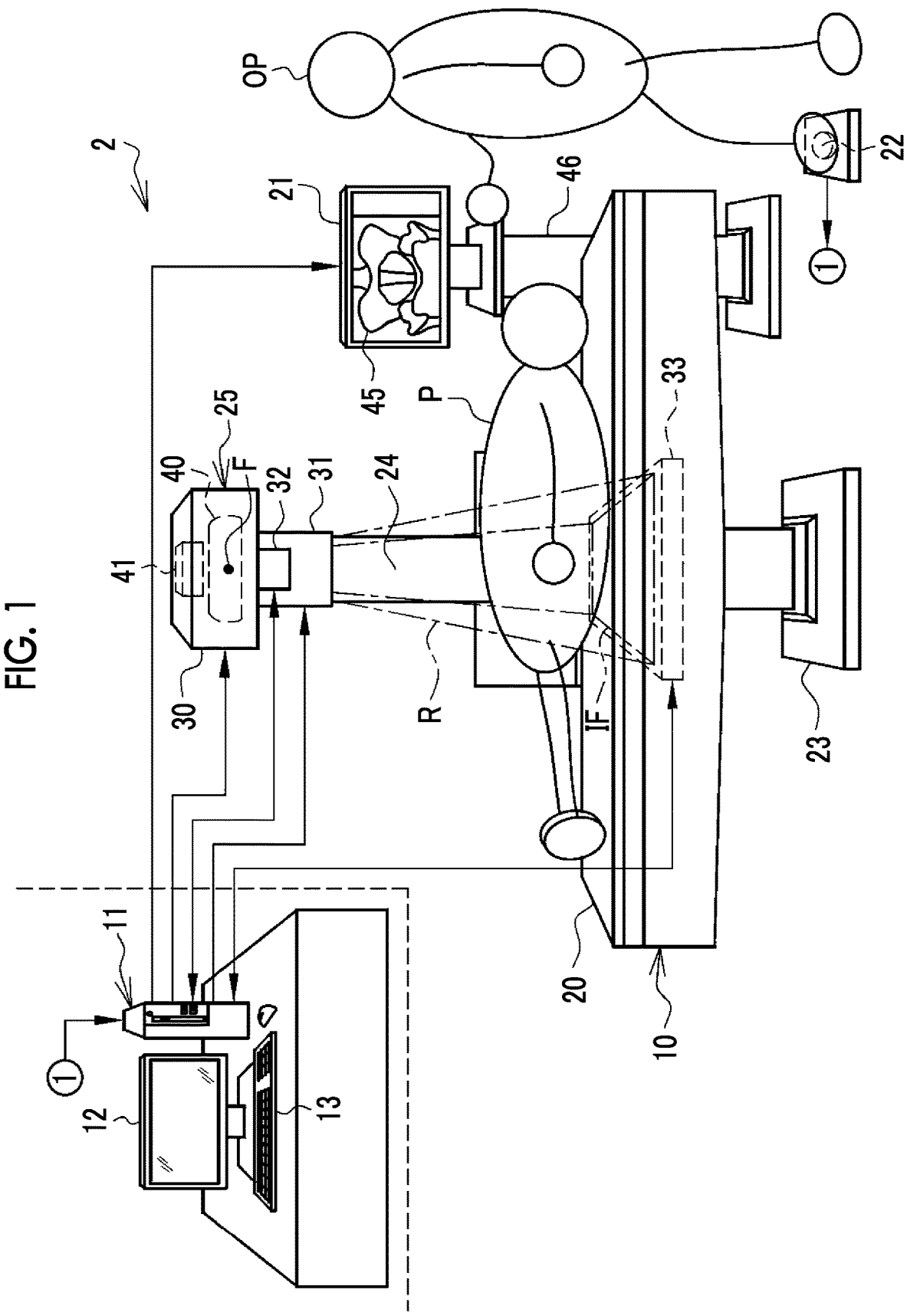
FIG. 1 is a diagram showing a radioscopy system.

In FIG. 1, a radioscopy system 2 comprises a radioscopy apparatus 10 and a console 11. The radioscopy apparatus 10 is provided in, for example, an operation room of a medical facility. The operation room is a room where an operator OP, such as a radiographer or a physician, performs an operation, such as a gastric barium test, cystography, or orthopedic reduction, to a patient P. The radioscopy apparatus 10 performs radioscopy to the patient P under operation. The patient P is an example of a "subject" according to the technique of the present disclosure.

The console 11 is an example of a "processing apparatus" according to the technique of the present disclosure, and is provided in, for example, a control room next to the operation room. The console 11 controls the operation of each unit of the radioscopy apparatus 10. The console 11 is, for example, a desktop personal computer, and has a display 12 and an input device 13, such as a keyboard or a mouse. The display 12 displays an imaging order or the like from a radiology information system (RIS). The input device 13 is operated by the operator OP in designating an imaging menu corresponding to the imaging order, or the like.

The radioscopy apparatus 10 has an imaging table 20, an operator monitor 21, a foot switch 22, and the like. The imaging table 20 is supported on a floor surface of the operation room by a stand 23. A radiation generation unit 25 is attached to the imaging table 20 through a post 24. The radiation generation unit 25 is constituted of a radiation source 30, a collimator 31, and a distance measurement camera 32. A radiation detector 33 is incorporated in the imaging table 20.

The radiation source 30 has a radiation tube 40. The radiation tube 40 emits radiation R, such as X-rays or γ-rays, and irradiates the patient P lying on the imaging table 20 with the radiation R, for example. The radiation tube 40 is provided with a filament, a target, a grid electrode, and the like (all are not shown). A voltage is applied between the filament as a cathode and the target as an anode from a voltage generator 41. The voltage that is applied between the filament and the target is referred to as a tube voltage. The filament discharges thermoelectrons according to the applied tube voltage toward the target. The target radiates the radiation R with collision of the thermoelectrons from the filament. The grid electrode is disposed between the filament and the target. The grid electrode changes a flow rate of the thermoelectrons from the filament toward the target depending on the voltage applied from the voltage generator 41. The flow rate of the thermoelectrons from the filament toward the target is referred to as a tube current. The tube voltage and the tube current are set as irradiation conditions (see FIG. 8) along with an irradiation time.

The collimator 31 and the distance measurement camera 32 are attached to a lower portion of the radiation source 30. The collimator 31 limits an irradiation field IF of the radiation R generated from the radiation tube 40. For example, the collimator 31 has a configuration in which four shield plates formed of lead or the like shielding the radiation R are disposed on respective sides of a quadrangle, and an emission opening of the quadrangle transmitting the radiation R is formed in a center portion. The collimator 31 changes the positions of the shield plates to change an opening degree of the emission opening, and accordingly, changes the irradiation field IF.

The distance measurement camera 32 is a camera that measures a distance to object surface using a time-of-flight (TOF) system. The distance measurement camera 32 is an example of a "body thickness measurement sensor" according to the technique of the present disclosure. The distance measurement camera 32 is viewed to be substantially as the same position as the radiation source 30, more exactly, a focus F of the radiation tube 40 at which the radiation R is generated, as viewed from the patient P side. For this reason, the distance measurement camera 32 may measure a distance between the radiation source 30 and an object surface. The object surface may be, for example, a body surface of the patient P or a surface of the imaging table 20. A distance between the focus F and the distance measurement camera 32 may be measured in advance, and a result obtained by adding the distance measured in advance between the focus F and the distance measurement camera 32 to the distance measured by the distance measurement camera 32 may be set as the distance between the radiation source 30 and the object surface. In the example, the distance between the radiation source 30 and the surface of the imaging table 20 is invariable.

The radiation detector 33 has a configuration in which a plurality of pixels that are sensitive to the radiation R or visible light converted from the radiation R by a scintillator to generate signal charge are arranged. Such a radiation detector 33 is referred to as a flat panel detector (FPD). The radiation detector 33 detects the radiation R emitted from the radiation tube 40 and transmitted through the patient P, and outputs a radiographic image 45. The radiation detector 33 transmits the radiographic image 45 to the console 11. The radiographic image 45 is also referred to as a perspective image.

The operator monitor 21 is supported on the floor surface of the operation room by a stand 46. The radiographic image 45 that is output from the radiation detector 33 and is subjected to various kinds of image processing with the console 11 is displayed on the operator monitor 21 in a form of video in real time.

The foot switch 22 is a switch for the operator OP giving an instruction to start and end radioscopy while being seated in the operation room. In a case where the operator OP depresses the foot switch 22 with a foot, radioscopy is started. Then, while the operator OP is depressing the foot switch 22 with the foot, radioscopy is continued. In a case where the operator OP releases the foot from the foot switch 22, and the depression of the foot switch 22 is released, radioscopy ends.

In a case where the foot switch 22 is depressed with the foot of the operator OP, the filament of the radiation tube 40 is pre-heated, and simultaneously the rotation of the target is started. After the filament reaches a specified temperature, and the target is at a specified rotation speed, the tube voltage is applied from the voltage generator 41, and the radiation R is generated from the radiation tube 40.

Figure 2:
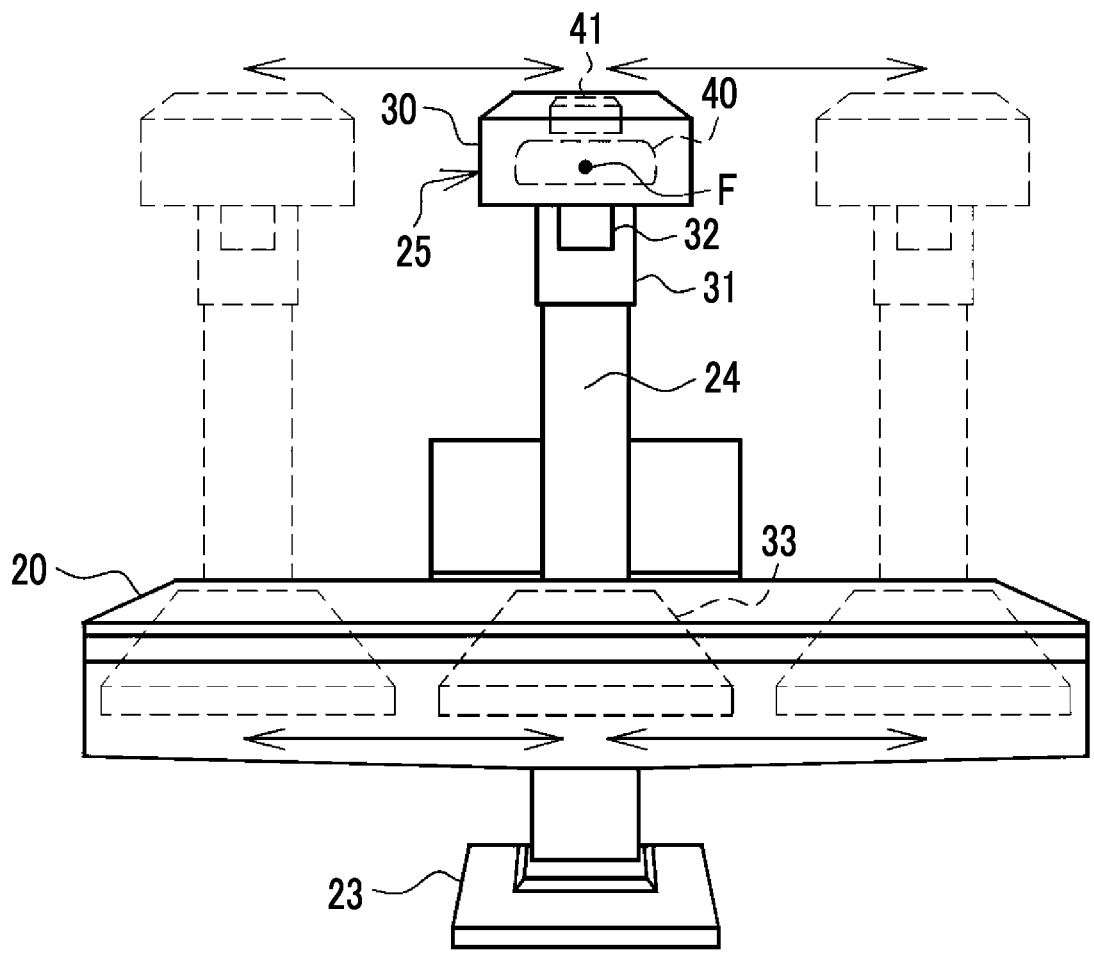
FIG. 2 is a diagram showing a manner in which a radiation generation unit and a radiation detector reciprocate along a longitudinal direction of an imaging table.

As shown in FIG. 2, not only the post 24 but also the radiation generation unit 25 can reciprocate along a longitudinal direction of the imaging table 20 by a movement mechanism (not shown), such as a motor. The radiation detector 33 can also reciprocate along the longitudinal direction of the imaging table 20 in conjunction with the movement of the radiation generation unit 25. The radiation detector 33 is moved to a facing position where the center thereof coincides with the focus F of the radiation tube 40. The imaging table 20 is provided with a control panel (not shown) for inputting an instruction to move the radiation generation unit 25 and the radiation detector 33. The operator OP inputs an instruction through the control panel and moves the radiation generation unit 25 and the radiation detector 33 to desired positions. The radiation generation unit 25 and the radiation detector 33 can be controlled by remote control by a control console (not shown) from the control room.

Figure 3A:
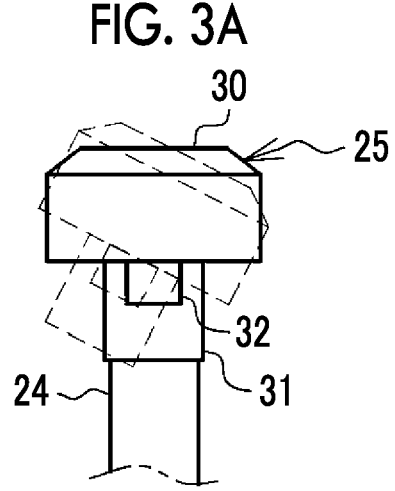
FIGS. 3A and 3B are diagrams showing a manner in which an angle of the radiation generation unit is changed.
Figure 3B:
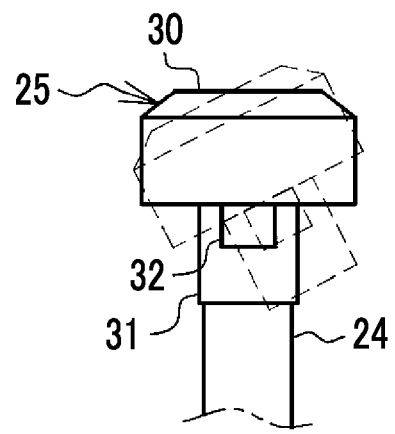

As shown in FIGS. 3A and 3B, the radiation generation unit 25 can change an angle right and left with respect to the post 24 with a hand of the operator OP. A changeable maximum angle is, for example, 90° right and left. The changing of the angle of the radiation generation unit 25 with respect to the post 24 can be controlled by remote control from the control room.

Figure 4:
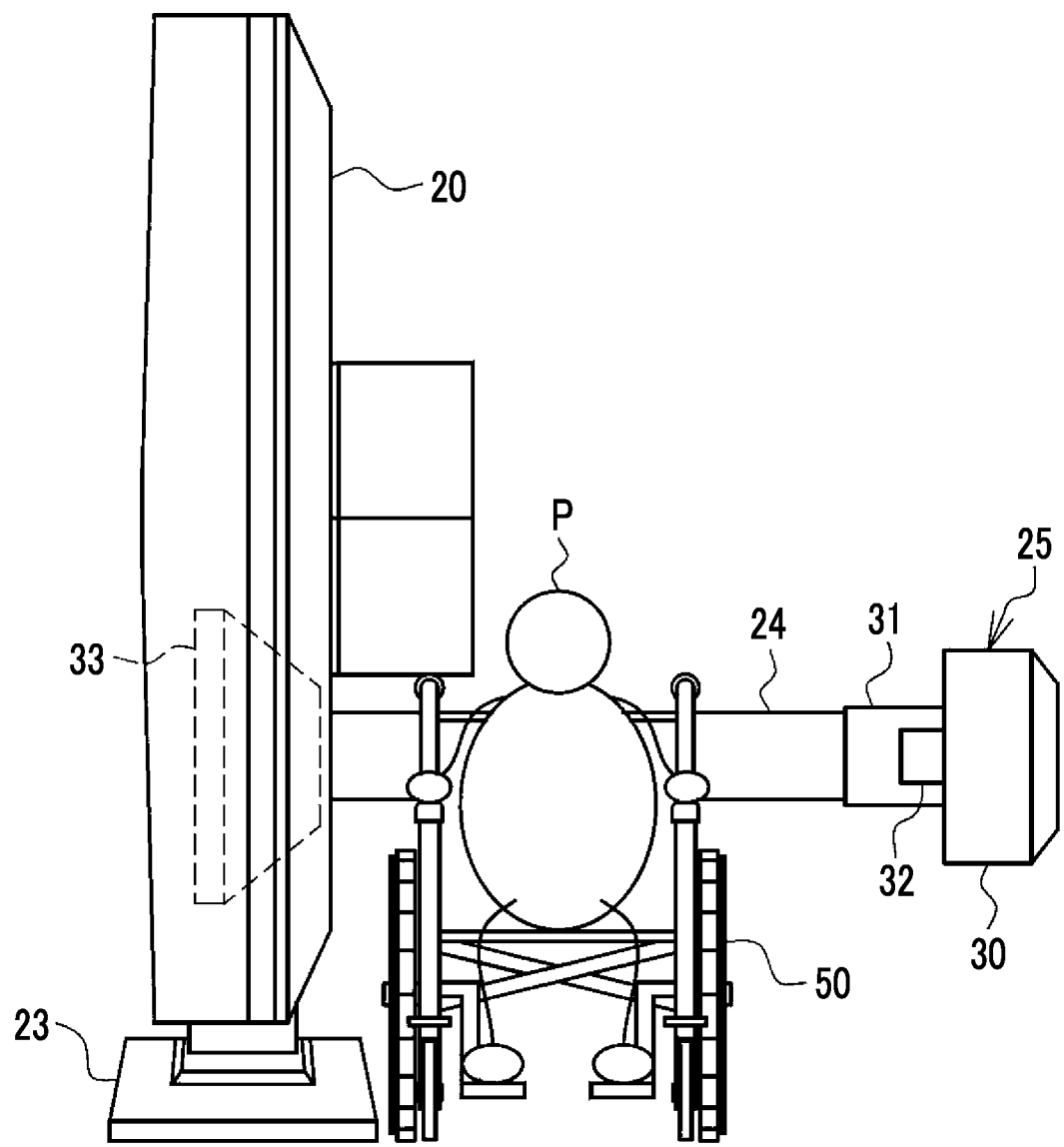
FIG. 4 is a diagram showing a manner in which radioscopy is performed on a patient in a wheelchair with an imaging table and a post in an upright state.
Figure 5:
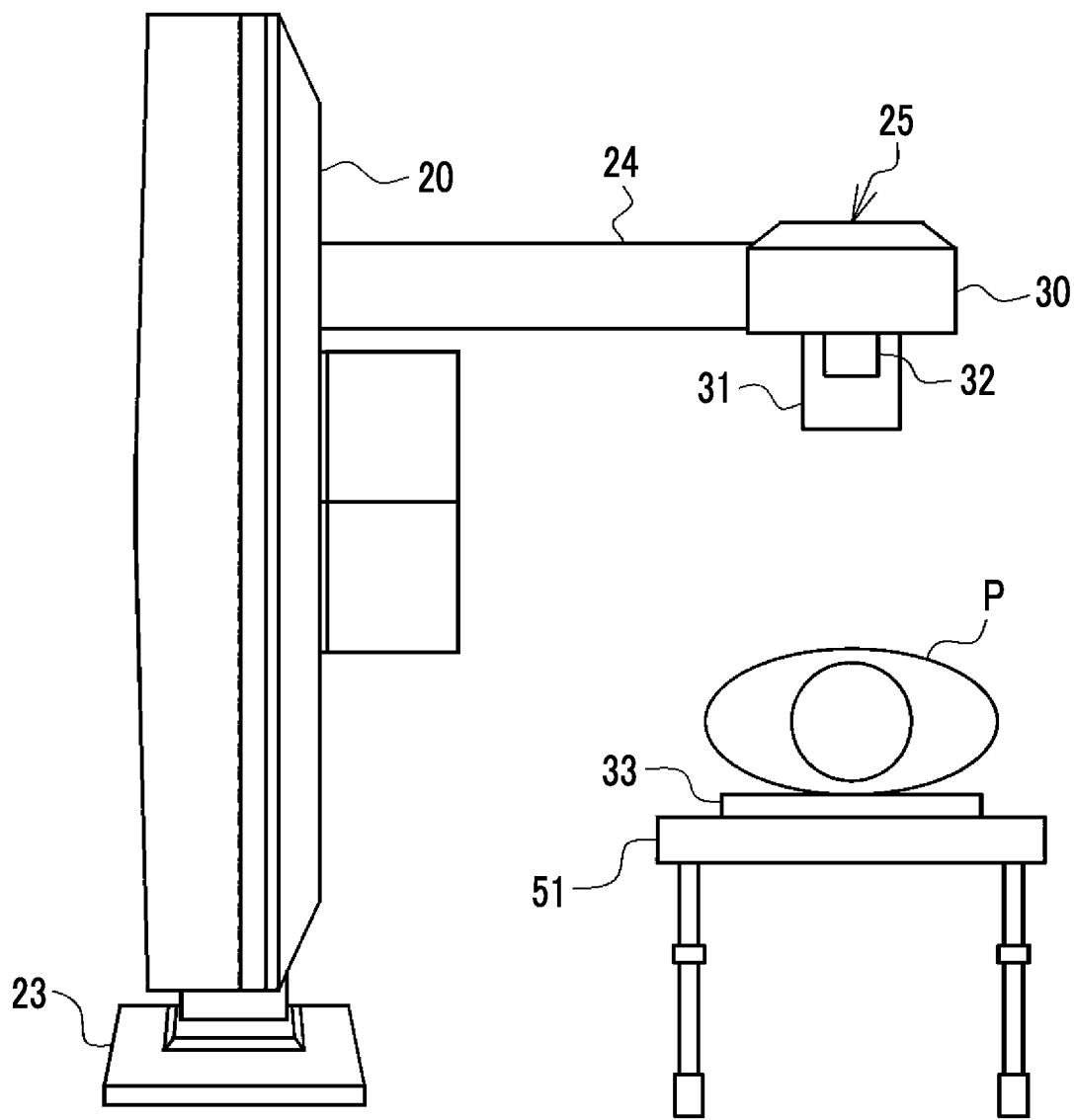
FIG. 5 is a diagram showing a manner in which radioscopy is performed on a patient on a stretcher with the imaging table and the post in the upright state.

The imaging table 20 and the post 24 can rotate between a decubitus state shown in FIGS. 1 and 2 and an upright state shown in FIGS. 4 and 5 by a rotation mechanism (not shown), such as a motor. The decubitus state is a state in which the surface of the imaging table 20 is parallel to the floor surface and the post 24 is perpendicular to the floor surface. On the contrary, the upright state is a state in which the surface of the imaging table 20 is perpendicular to the floor surface, and the post 24 is parallel to the floor surface. In the upright state, not only radioscopy on the patient P in an upright posture, but also radioscopy on the patient P in a wheelchair 50 as shown in FIG. 4 can be performed. In the upright state, radioscopy on the patient P on a stretcher 51 as shown in FIG. 5 can also be performed. In the case of FIG. 5, the radiation detector 33 is detached from the imaging table 20 and is set between the patient P and the stretcher 51.

Figure 6:
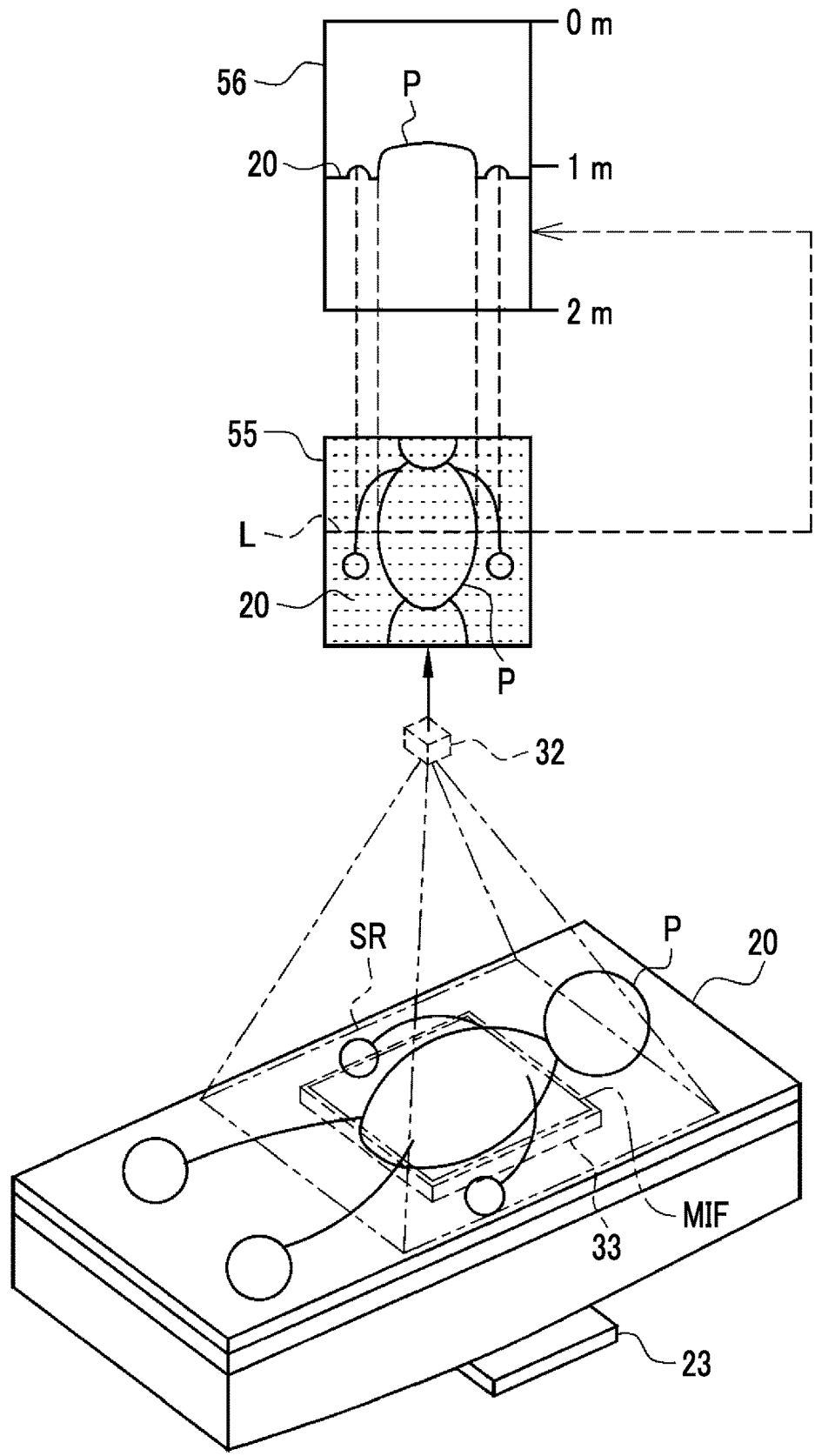
FIG. 6 is a diagram showing a manner in which the patient and the periphery of the patient are imaged with a distance measurement camera and a distance image representing a distance between a radiation source and an object surface is output.

As shown in FIG. 6, the distance measurement camera 32 images a rectangular imaging range SR including the patient P and the periphery of the patient P, and outputs a distance image 55. The imaging range SR is a range sufficiently wider than a maximum irradiation field MIF of the radiation R, and covers the entire maximum irradiation field MIF of the radiation R.

The distance image 55 is an image in which an attachment position of the distance measurement camera 32, that is, a position of the radiation source 30 is represented as 0 m, as illustrated with a profile 56 of a line L at the center. The distance image 55 has, as a pixel value of each pixel, a distance between the radiation source 30 and a surface of an object in the imaging range SR, such as the patient P or the imaging table 20.

Figure 7:
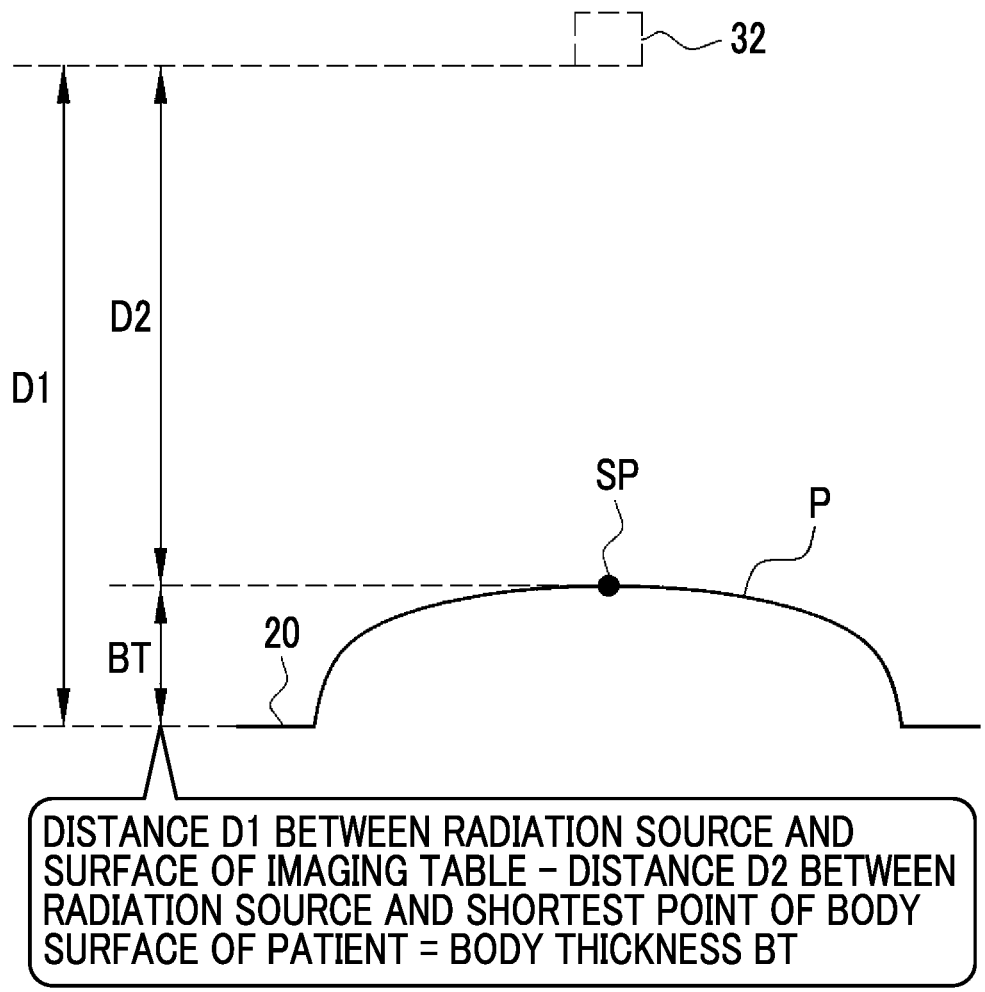
FIG. 7 is a diagram showing a manner in which a body thickness of the patient is calculated based on a distance between the radiation source and a surface of the imaging table and a distance between the radiation source and a shortest point of a body surface of the patient.

As shown in FIG. 7, in a case where the distance radiation source 30 (distance measurement camera 32) and the surface of the imaging table 20 is D1, and the distance between the radiation source 30 (distance measurement camera 32) and a shortest point SP of a body surface of the patient P is D2, a body thickness BT of the patient P can be calculated by Expression (1) described below.

$$BT = D1 - D2 \quad (1)$$

As described above, the distance D1 between the radiation source 30 and the surface of the imaging table 20 is invariable. For this reason, in a case where the distance D2 between the radiation source 30 and the shortest point SP of the body surface of the patient P is derived from the distance image 55, the body thickness BT is simply calculated. In the case of FIG. 5 where radioscopy is performed on the patient P on the stretcher 51, the body thickness BT is calculated by further subtracting a thickness of the radiation detector 33.

The distance D2 is derived as follows, for example. First, the distance D1 is invariable and known, and thus, a region of the distance image 55 having a distance less than the distance D1 as a pixel value is recognized as a region of the patient P. Next, a position at the shortest distance in the recognized region of the patient P, that is, the shortest point SP is searched, and a pixel value of the searched shortest point SP is derived as the distance D2. As in the example, in a case where the distance D1 between the radiation source 30 and the surface of the imaging table 20 is invariable, the distance D2 between the radiation source 30 and the shortest point SP of the body surface of the patient P may be regarded as the body thickness BT.

Figure 8:
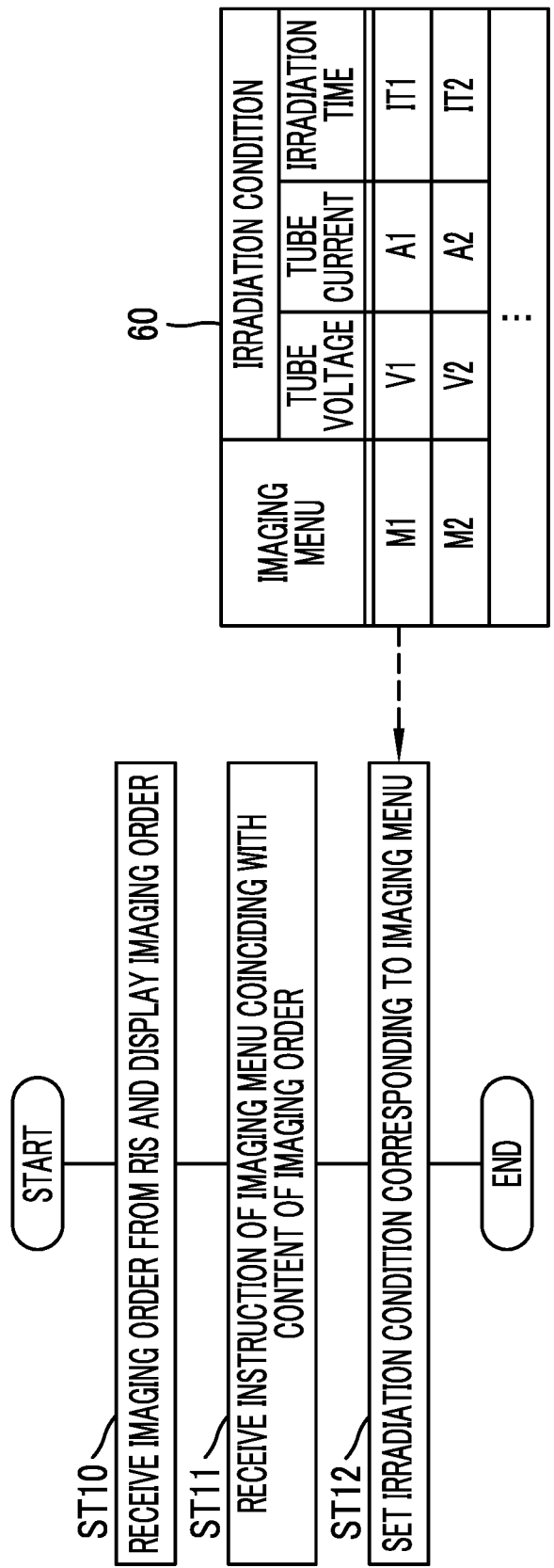
FIG. 8 is a flowchart showing a procedure for setting irradiation conditions.

As shown in FIG. 8, prior to radioscopy, the console 11 receives the imaging order from the RIS and displays the imaging order on the display 12 (Step ST10). In the imaging order, patient identification data (ID) for identifying the patient P, an instruction of an operation by a physician of a treatment department who issues the imaging order, and the like are registered. The operator OP confirms the content of the imaging order through the display 12.

The console 11 displays a plurality of kinds of imaging menus prepared in advance on the display 12 in an alternatively selectable form. The operator OP selects one imaging menu coinciding with the content of the imaging order through the input device 13. With this, the console 11 receives an instruction of the imaging menu (Step ST11). The console 11 sets irradiation conditions corresponding to the instructed imaging menu with reference to an irradiation condition table 60 (Step ST12). After selecting the imaging menu, the operator OP performs positioning and the like of the radiation source 30, the radiation detector 33, and the patient P, and depresses the foot switch 22 with the foot to start radioscopy. The irradiation conditions have content where the irradiation of the radiation R is performed with an extremely low dose compared to a case where general radiography is performed.

Figure 9:
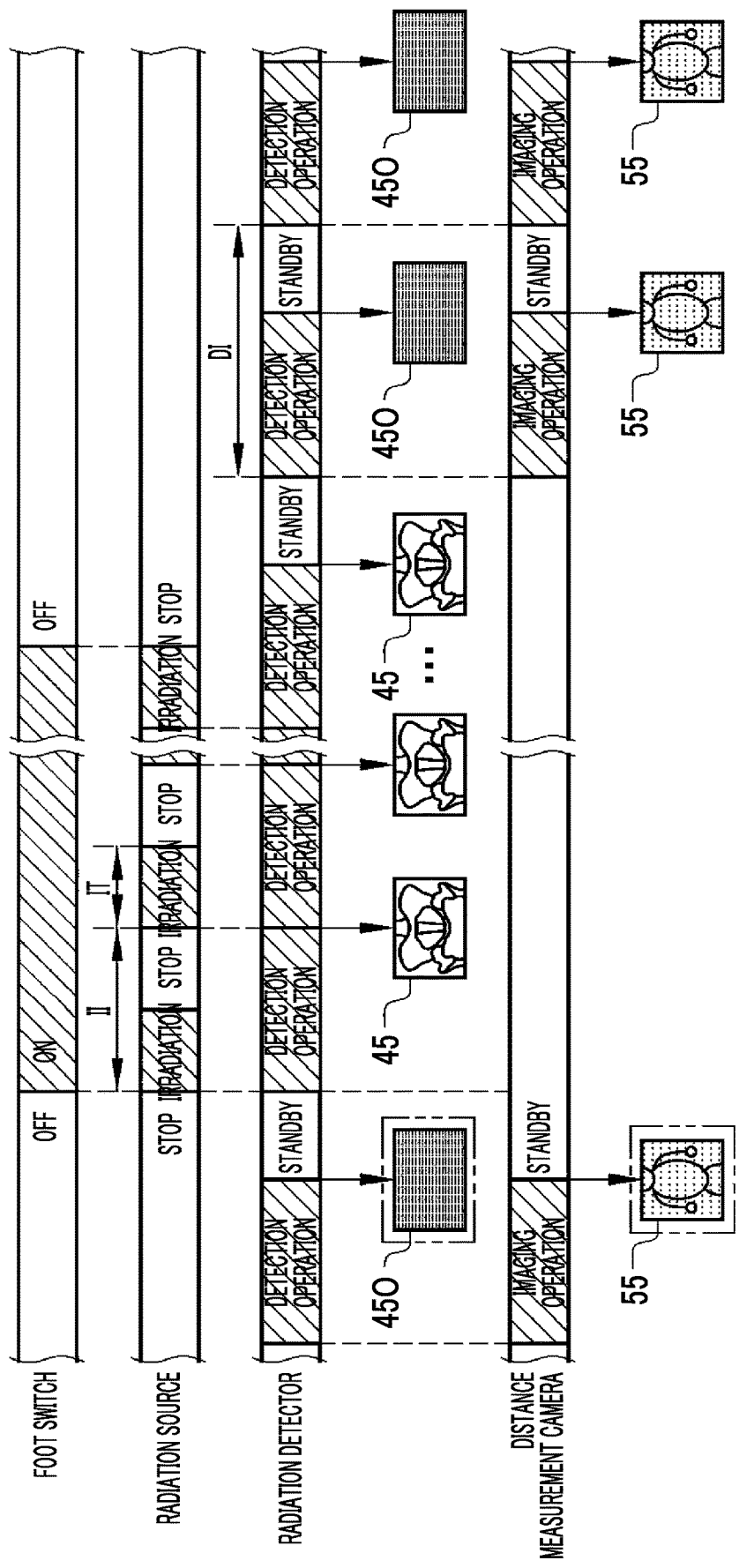
FIG. 9 is a timing chart showing an operation timing of each unit in radioscopy.

As shown in FIG. 9, the radiation source 30 starts the irradiation of the radiation R set under the irradiation conditions in synchronization with a timing at which the foot switch 22 is depressed with the foot of the operator OP, that is, a timing from off to on in the drawing. The radiation source 30 repeats the irradiation and the stop of the radiation R at an irradiation interval II set in advance while the foot switch 22 is being depressed with the foot of the operator OP. That is, the radiation source 30 continuously irradiates the patient P with the radiation R. The radiation source 30 stops the irradiation of the radiation R in a case where the depression of the foot switch 22 is released. The irradiation interval II is variable with, for example, about 0.033 seconds (30 frames per second (fps) as converted into a frame rate) as an upper limit. A sign IT indicates an irradiation time set under the irradiation conditions.

The radiation detector 33 starts a detection operation in synchronization with an irradiation start timing of the radiation R. The radiation detector 33 repeats the detection operation while the foot switch 22 is being depressed with the foot of the operator OP, and the irradiation of the radiation R is being performed from the radiation source 30 in a pulsed manner. With the repetitive detection operations during the irradiation of the radiation R, the radiation detector 33 outputs the radiographic image 45 at the irradiation interval II.

The radiation detector 33 performs the detection operation even though the depression of the foot switch 22 is released, and the irradiation of the radiation R is not performed from the radiation source 30. The radiation detector 33 repeatedly performs the detection operation in a state in which the irradiation of the radiation R is not performed, at a detection interval DI set in advance. The detection interval DI is a time sufficiently longer than the irradiation interval II of the radiation R, and is, for example, one minute. With the detection operation in a state in which the irradiation of the radiation R is not performed, the radiation detector 33 outputs a radiographic image for offset correction (hereinafter, referred to as an offset correction image) 45O. The radiation detector 33 transmits the offset correction image 45O to the console 11.

The distance measurement camera 32 performs an imaging operation of the distance image 55 in synchronization with a detection operation of the offset correction image 45O of the radiation detector 33. In other words, the distance measurement camera 32 measures the body thickness of the patient P in synchronization with a timing at which the radiation detector 33 outputs the offset correction image 45O.

In FIG. 9, although an aspect where the irradiation of the radiation R is performed in a pulsed manner has been exemplified, the present disclosure is not limited thereto. An aspect where the irradiation of the radiation is consecutively performed while the foot switch 22 is being depressed with the foot of the operator OP may be employed. Even in an aspect where the irradiation of the radiation R is performed in a pulsed manner or an aspect where the irradiation of the radiation R is consecutively performed, the fact remains that the patient P is continuously irradiated with the radiation R.

Figure 10:
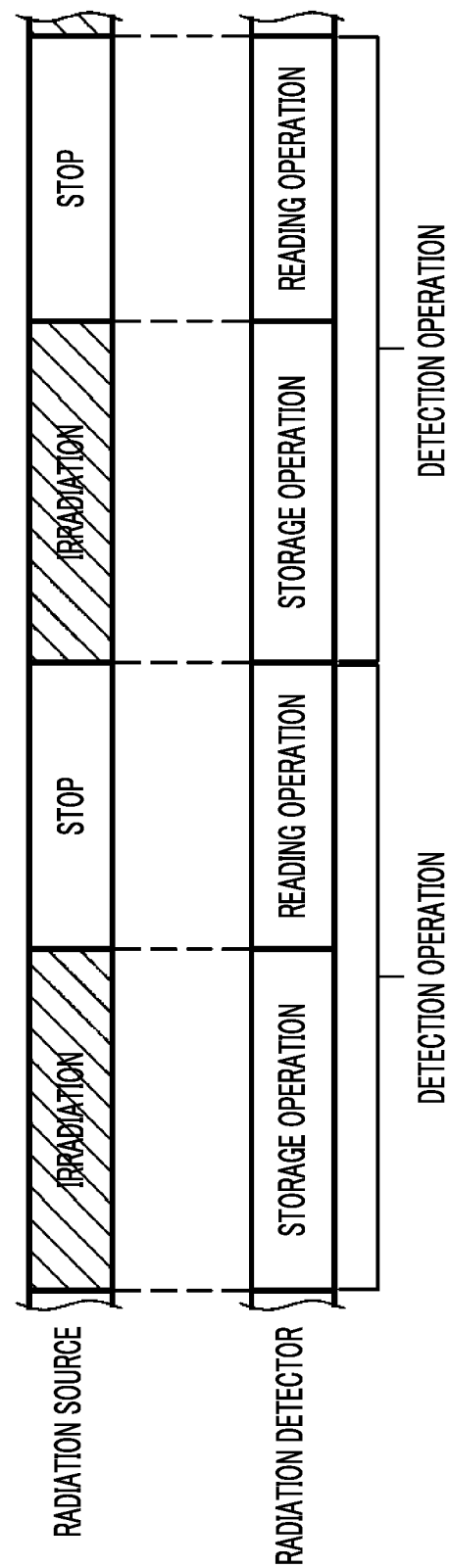
FIG. 10 is a timing chart showing specific content of a detection operation.

As shown in FIG. 10, the detection operation is constituted of a storage operation and a reading operation. The storage operation is an operation to store signal charge in a pixel, and is started in synchronization with the irradiation start timing of the radiation R. The reading operation is an operation to read the signal charge stored in the pixel and to output the signal charge as the radiographic image 45, and is started in synchronization with an irradiation end timing of the radiation R.

Figure 11:
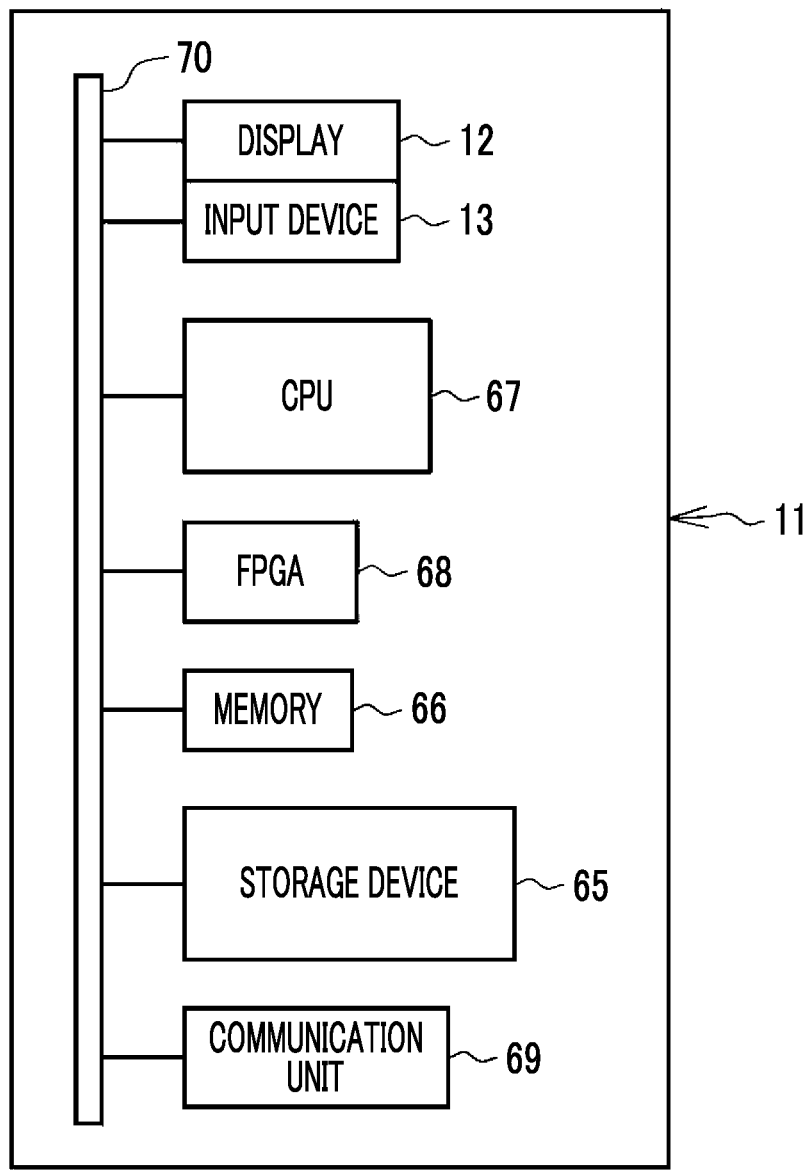
FIG. 11 is a block diagram of a computer constituting a console.

In FIG. 11, the computer constituting the console 11 comprises a storage device 65, a memory 66, a central processing unit (CPU) 67, a field programmable gate array (FPGA) 68, and a communication unit 69, in addition to the display 12 and the input device 13. Such devices and units are connected to one another through a busline 70.

The storage device 65 is a hard disk drive that is incorporated in the computer constituting the console 11 or a connected to the computer through a cable and a network. Alternatively, the storage device 65 is a disk array in which a plurality of hard disk drives are mounted. In the storage device 65, a control program, such as an operating system, various application programs, various kinds of data associated with such programs, and the like are stored. A solid state drive may be used instead of the hard disk drive.

The memory 66 is a work memory on which the CPU 67 executes processing. The CPU 67 loads a program stored in the storage device 65 to the memory 66 to execute processing compliant with the program. With this, the CPU 67 integrally controls the operation of each unit of the radioscopy apparatus 10. The communication unit 69 takes charge of communication of various kinds of information with each unit of the radioscopy apparatus 10.

Figure 12:
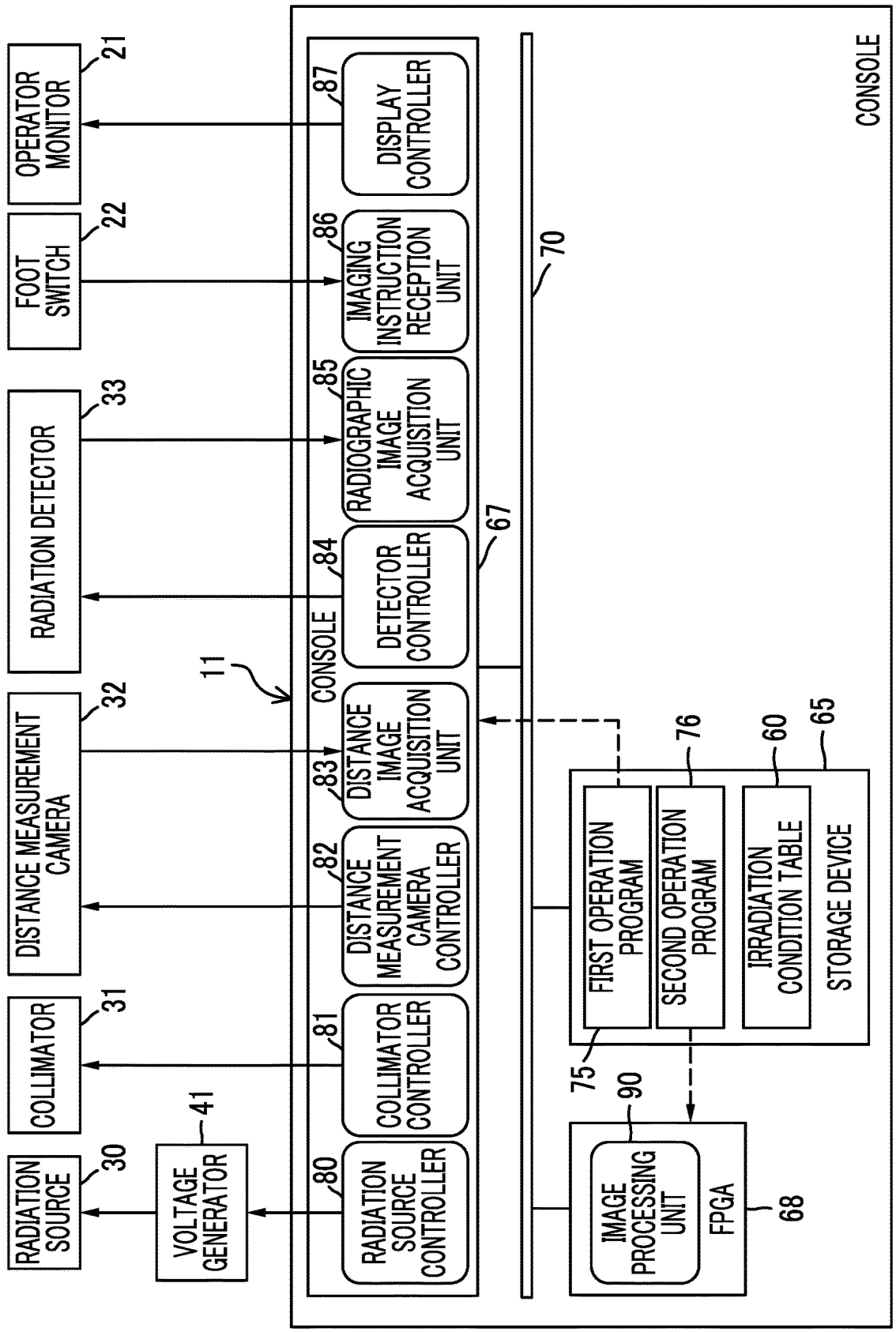
FIG. 12 is a block diagram showing functions of a CPU and an FPGA of the console.

In FIG. 12, in the storage device 65 of the console 11, a first operation program 75 and a second operation program 76 are stored. The first operation program 75 and the second operation program 76 are an application program that causes the computer constituting the console 11 to function as a "processing apparatus" according to the technique of the present disclosure. That is, the first operation program 75 and the second operation program 76 are an example of an "operation program for a processing apparatus" according to the technique of the present disclosure. In the storage device 65, the irradiation condition table 60 is also stored.

In a case where the first operation program 75 is activated, the CPU 67 of the computer constituting the console 11 functions as a radiation source controller 80, a collimator controller 81, a distance measurement camera controller 82, a distance image acquisition unit 83, a detector controller 84, a radiographic image acquisition unit 85, an imaging instruction reception unit 86, and a display controller 87 in cooperation with the memory 66 and the like. In a case where the second operation program 76 is activated, the FPGA 68 of the computer constituting the console 11 functions as an image processing unit 90. The CPU 67 and the FPGA 68 are an example of a "processor" according to the technique of the present disclosure.

The radiation source controller 80 controls the operation of the radiation source 30 to control the irradiation of the radiation R. The radiation source controller 80 reads the irradiation conditions corresponding to the imaging menu selected by the operator OP from the irradiation condition table 60 and sets the read irradiation condition in the voltage generator 41. The radiation source controller 80 causes the irradiation of the radiation R from the radiation source 30 through the voltage generator 41 under the set irradiation conditions. The radiation source controller 80 outputs irradiation start and stop timings of the radiation R to the detector controller 84.

The radiation source controller 80 performs auto brightness control (ABC). As known in the art, the ABC is feedback control where, to maintain the brightness of the radiographic image 45 within a given range, during radioscopy, the tube voltage, the tube current, an irradiation time IT, the irradiation interval II, and the like given to the radiation tube 40 are finely adjusted based on a brightness value (for example, an average value of brightness values of a center region of the radiographic image 45) of the radiographic image 45 sequentially output from the radiation detector 33. With the ABC, the brightness of the radiographic image 45 is prevented from being extremely changed due to body movement or the like of the patient P or the radiographic image 45 is prevented from being hardly observed.

The collimator controller 81 controls the operation of the shield plates of the collimator 31 and adjusts the opening degree of the emission opening formed by the shield plates to an opening degree corresponding to the imaging menu selected by the operator OP. The opening degree of the emission opening can also be adjusted by the operator OP through a control panel (not shown) provided in the collimator 31 itself.

The distance measurement camera controller 82 controls the operation of the distance measurement camera 32. Specifically, the distance measurement camera controller 82 makes the distance measurement camera 32 perform an imaging operation of the distance image 55 in synchronization with the timing at which the radiation detector 33 outputs the offset correction image 45O in a case where the irradiation of the radiation R is not performed.

The distance image acquisition unit 83 acquires the distance image 55 from the distance measurement camera 32. The distance image acquisition unit 83 outputs the distance image 55 to the image processing unit 90.

The detector controller 84 controls the operation of the radiation detector 33. The detector controller 84 makes the radiation detector 33 perform the storage operation in a case where the irradiation of the radiation R is started in radioscopy. The detector controller 84 makes the radiation detector 33 perform the reading operation in a case where the irradiation of the radiation R is stopped in radioscopy. With this, the radiographic image 45 is output from the radiation detector 33.

The detector controller 84 makes the radiation detector 33 perform the detection operation at the detection interval DI in a case where the irradiation of the radiation R is not performed. With this, the offset correction image 45O is output from the radiation detector 33.

The radiographic image acquisition unit 85 acquires the radiographic image 45 and the offset correction image 45O from the radiation detector 33. That is, the radiographic image acquisition unit 85 takes charge of "image acquisition processing" according to the technique of the present disclosure. The radiographic image acquisition unit 85 outputs the radiographic image 45 and the offset correction image 45O to the image processing unit 90.

The imaging instruction reception unit 86 receives an instruction to start and end radioscopy through the foot switch 22. The imaging instruction reception unit 86 outputs the received instruction to the radiation source controller 80 and the detector controller 84.

The display controller 87 performs control for displaying the radiographic image 45 subjected to various kinds of image processing with the image processing unit 90 on the operator monitor 21. The display controller 87 also performs control for displaying the imaging order, the imaging menu, and the like on the display 12.

The image processing unit 90 executes various kinds of image processing on the radiographic image 45. For example, the image processing unit 90 executes offset correction processing, sensitivity correction processing, defective pixel correction processing, and the like as the image processing.

The offset correction processing is processing for subtracting the offset correction image 45O output in a state in which the irradiation of the radiation R is not performed, from the radiographic image 45 output by radioscopy in units of pixels. In the offset correction processing, the latest offset correction image 45O most recently acquired by the radiographic image acquisition unit 85 and surrounded by a frame of a two-dot chain line in FIG. 9 is used. The image processing unit 90 executes the offset correction processing to remove fixed pattern noise due to dark charge or the like from the radiographic image 45.

The sensitivity correction processing is processing for correcting variation in sensitivity of each pixel of the radiation detector 33, variation or the like in output characteristic of a circuit that reads the signal charge, and the like based on sensitivity correction data. The defective pixel correction processing is processing of linearly interpolating a pixel value of a defective pixel with a pixel value of a surrounding normal pixel based on information of a defective pixel having an abnormal pixel value generated during shipment, during a periodic inspection, or the like. The image processing unit 90 outputs the radiographic image 45 subjected to various kinds of image processing to the display controller 87.

Figure 13:
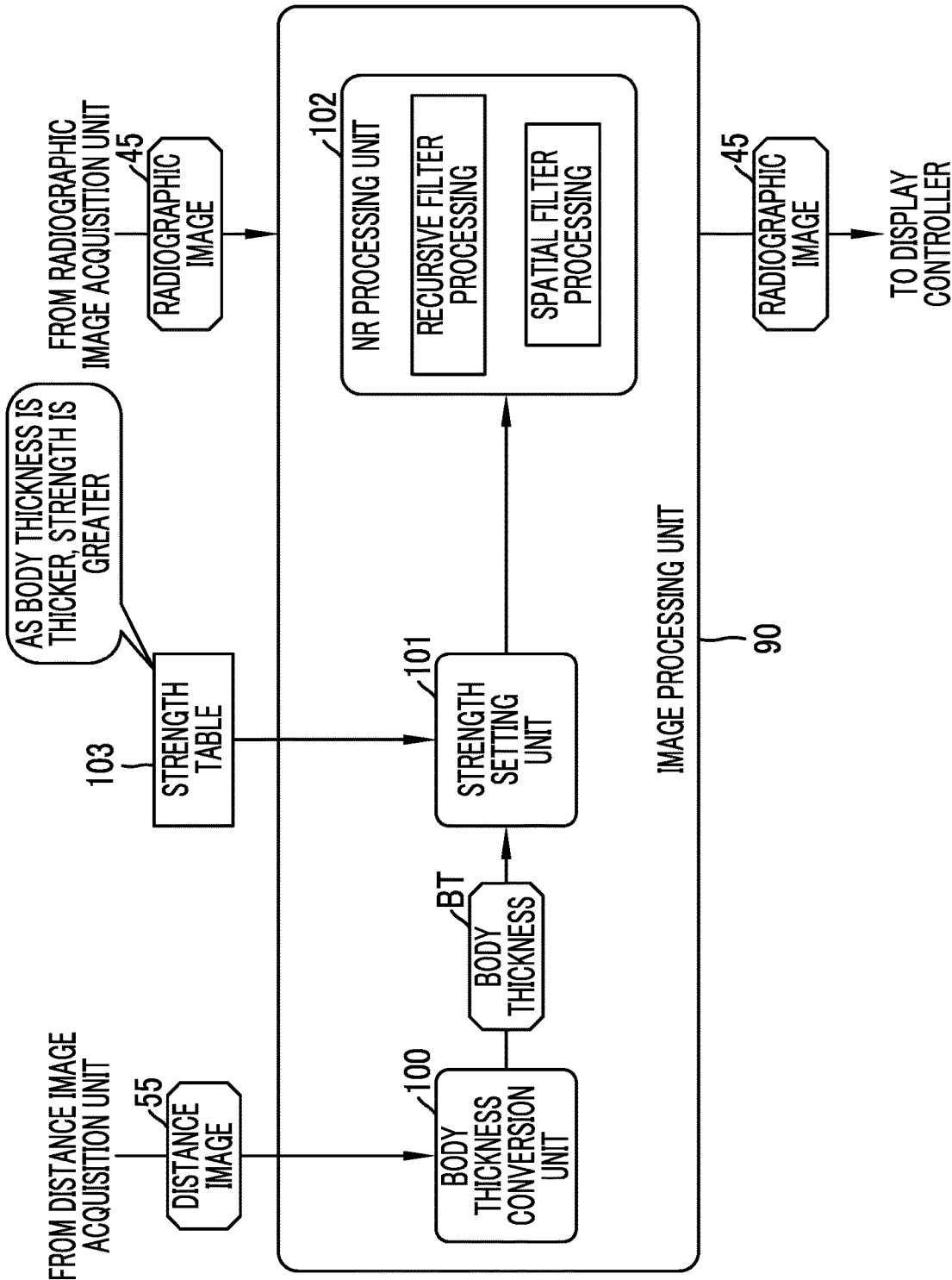
FIG. 13 is a block diagram showing details of an image processing unit.

As shown in FIG. 13, the image processing unit 90 has a body thickness conversion unit 100, a strength setting unit 101, and an NR processing unit 102, in addition to the units (not shown) that perform various kinds of correction processing described above.

The distance image 55 is input to the body thickness conversion unit 100 from the distance image acquisition unit 83. As shown in FIG. 7 and Expression (1), the body thickness conversion unit 100 subtracts the distance D2 between the radiation source 30 and the shortest point SP of the body surface of the patient P from the distance D1 between the radiation source 30 and the surface of the imaging table 20 to calculate the body thickness BT of the patient P. That is, the body thickness conversion unit 100 takes charge of "body thickness acquisition processing" according to the technique of the present disclosure. The body thickness conversion unit 100 outputs the calculated body thickness BT to the strength setting unit 101.

The strength setting unit 101 sets strength of NR processing by the NR processing unit 102 corresponding to the body thickness BT converted by the body thickness conversion unit 100 based on the distance image 55 acquired immediately before radioscopy is started and surrounded by the frame of a two-dot chain line in FIG. 9. The strength setting unit 101 refers to a strength table 103 in setting the strength. The strength table 103 is stored in the storage device 65, and has the content that the thicker the body thickness BT, the stronger the strength of the NR processing. For this reason, the strength setting unit 101 sets the strength of the NR processing to be stronger as the body thickness BT is thicker. That is, the strength setting unit 101 takes charge of "strength setting processing" according to the technique of the present disclosure. The strength setting unit 101 outputs a setting result of the strength to the NR processing unit 102.

The NR processing unit 102 executes the NR processing on the radiographic image 45 with the strength set by the strength setting unit 101. That is, the NR processing unit 102 takes charge of "image processing" according to the technique of the present disclosure. The radiographic image 45 subjected to, for example, the offset correction processing, the sensitivity correction processing, and the defective pixel correction processing described above is input to the NR processing unit 102.

The NR processing unit 102 executes recursive filter processing and spatial filter processing as the NR processing. The recursive filter processing is processing shown in FIG. 14. Examples of the spatial filter processing include median filter processing shown in FIG. 15 and Gaussian filter processing shown in FIG. 16. Hereinafter, the outline of each kind of processing will be described in order.

Figure 14:
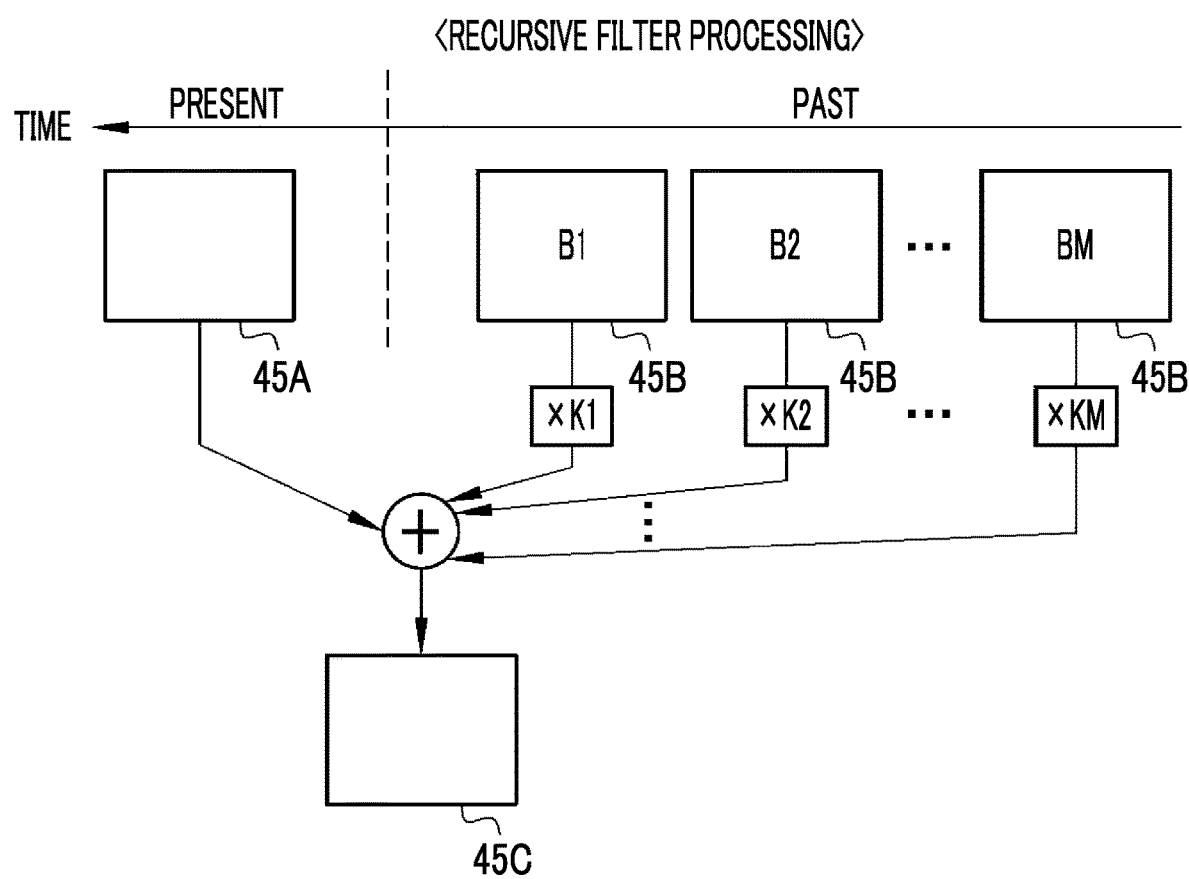
FIG. 14 is a diagram showing the outline of recursive filter processing.

As shown in FIG. 14, the recursive filter processing is processing of adding a past image 45B as the radiographic image 45 output further in the past than an processing target image 45A as the radiographic image 45 to be processed to the processing target image 45A and outputting a result as a radiographic image 45C subjected to the recursive filter processing. The past image 45B is multiplied by an appropriate weighting coefficient K before addition to the processing target image 45A. According to the recursive filter processing, noise of the processing target image 45A is reduced by the past image 45B. In the recursive filter processing, as the number of past images 45B (hereinafter, referred to as the number of added images) added to the processing target image 45A increases, the strength of the NR processing is stronger. As the value of the weighting coefficient K is greater, the strength of the NR processing is stronger.

FIG. 14 illustrates a manner in which a past image 45B (B1) output one frame before the processing target image 45A, a past image 45B (B2) output two frames before the processing target image 45A, . . . , and a past image 45B (BM) output M frames before the processing target image 45A are added to the processing target image 45A output at present. FIG. 14 also illustrates a manner in which the past image 45B (B1), the past image 45B (B2), . . . , and the past image 45B (BM) are multiplied by a weighting coefficient K1, a weighting coefficient K2, . . . , and a weighting coefficient KM, respectively, and then, are added. M is the number of added images.

Figure 15:
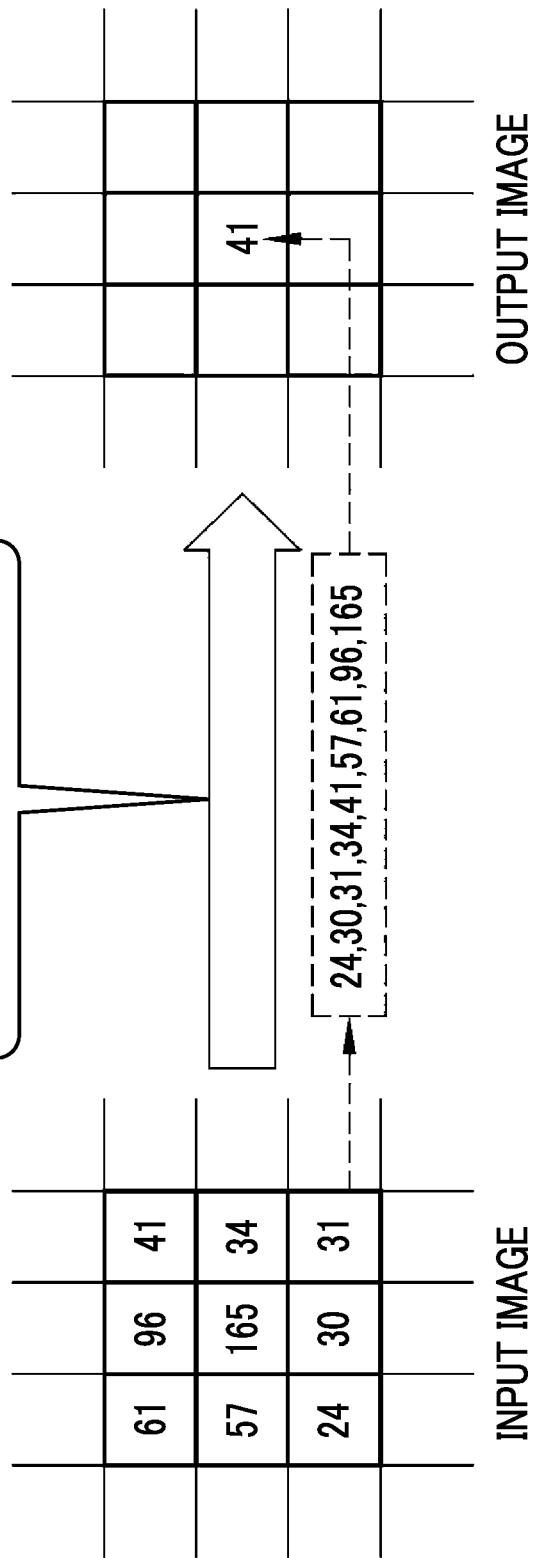
FIG. 15 is a diagram showing the outline of median filter processing.

As shown in FIG. 15, the median filter processing is processing described below. That is, on an input image shown on a left side of an arrow, for example, a median value of pixel values of a region of 3×3 pixels is extracted. Then, the extracted median value is replaced as a pixel value of a pixel of interest at the center of a region of 3×3 pixels of an output image shown on a right side of the arrow. The extraction of the median value and the replacement of the pixel value are performed to all pixels of the input image. The input image is, for example, the radiographic image 45C subjected to the recursive filter processing. According to the median filter processing, spike noise in the radiographic image 45 is effectively removed. According to the median filter processing, an edge of a structure in the radiographic image 45 is smoothed. In the median filter processing, as the size (also referred to as a size of a median filter or a kernel size) of a region of pixels for extracting a median value is greater, the strength of the NR processing is stronger.

FIG. 15 illustrates a case where the pixel values of the region of the 3×3 pixels of the input image are 61, 96, 41, 57, 165, 34, 24, 30, 31, and the median value is 41. The pixel value of the pixel of interest of the output image in this case is replaced from 165 of the input image with 41.

Figure 16:
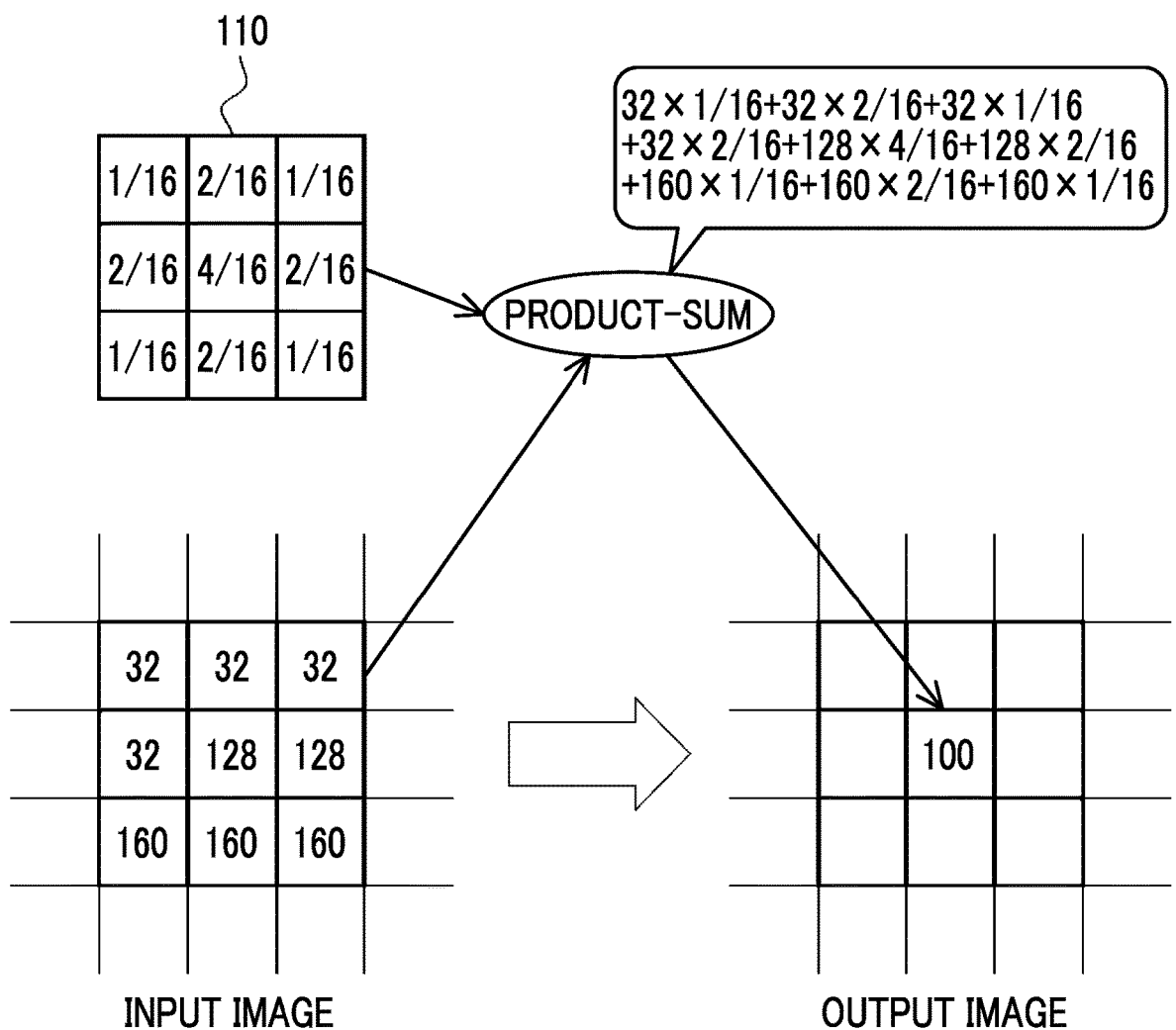
FIG. 16 is a diagram showing the outline of Gaussian filter processing.

As shown in FIG. 16, the Gaussian filter processing is processing described below. That is, a product-sum of each pixel value of, for example, a region of 3×3 pixels of an input image shown on a left side of an arrow and a coefficient of a Gaussian filter 110 having a size of 3×3 too is calculated. Then, the calculated product-sum is replaced in a pixel value of a pixel of interest at the center of a region of 3×3 pixels of an output image shown on a right side of the arrow. The calculation of the product-sum and the replacement of the pixel value are performed to all pixels of the input image. The input image is, for example, the radiographic image 45 subjected to the median filter processing. The coefficient of the Gaussian filter 110 is decided based on the Gaussian distribution. According to the Gaussian filter processing, noise in the radiographic image 45 is effectively removed. According to the Gaussian filter processing, an edge of a structure in the radiographic image 45 is more smoothed than the median filter processing. In the Gaussian filter processing, the greater the size (also referred to as a kernel size) of the Gaussian filter 110, the stronger the strength of the NR processing.

FIG. 16 illustrates a case where pixel values of the region of 3×3 pixels of the input image are 32, 32, 32, 32, 128, 128, 160, 160, and 160, and the coefficient of the Gaussian filter 110 is 1/16, 2/16, 1/16, 2/16, 4/16, 2/16, 1/16, 2/16, and 1/16. The pixel value of the pixel of interest of the output image in this case is replaced from 128 of the input image with 100.

The NR processing unit 102 executes such recursive filter processing and spatial filter processing on the radiographic image 45 from the radiation detector 33 to remove noise due to a low dose of the radiation R. Only the recursive filter processing or only the spatial filter processing may be executed. Alternatively, only the median filter processing or only the Gaussian filter processing may be executed.

In FIG. 17, in a strength table 103R for recursive filter processing, the number of added images and the weighting coefficient K to the body thickness BT are registered. In the number of added images, as the body thickness BT is thicker, a greater number is registered. Specifically, in a case where the body thickness BT is less than 10 cm, three is registered, in a case where the body thickness BT is equal to or greater than 10 cm and less than 15 cm, five is registered, in a case where the body thickness BT is equal to or greater than 15 cm and less than 20 cm, seven is registered, . . . In the weighting coefficient K, as the body thickness BT is thicker, a greater value is registered, except for the weighting coefficient K1 of 1. Specifically, in regard to the weighting coefficient K2, in a case where the body thickness BT is less than 10 cm, 0.5 is registered, in a case where the body thickness BT is equal to or greater than 10 cm and less than 15 cm, 0.8 is registered, in a case where the body thickness BT is equal to or greater than 15 cm and less than 20 cm, 0.85 is registered, . . . In this way, the strength table 103R for recursive filter processing has the content that the thicker the body thickness BT, the stronger the strength of the recursive filter processing. Accordingly, the strength setting unit 101 sets the strength of the recursive filter processing to be stronger as the body thickness BT is thicker. To reduce the influence of the past image 45B having a gap in time from the processing target image 45A, the weighting coefficient K is set to a smaller value as the past image 45B has a greater gap in time from the processing target image 45A.

In FIG. 18, in a strength table 103M for median filter processing, the size of a median filter to the body thickness BT is registered. In the size of the median filter, a greater size is registered as the body thickness BT is thicker. Specifically, in a case where the body thickness BT is less than 10 cm, 3×3 is registered, in a case where the body thickness BT is equal to or greater than 10 cm and less than 15 cm, 5×5 is registered, in a case where the body thickness BT is equal to or greater than 15 cm and less than 20 cm, 7×7 is registered, . . . In this way, similarly to the strength table 103 for recursive filter processing, the strength table 103M for median filter processing also has the content that the thicker the body thickness BT, the stronger the strength of the median filter processing. Accordingly, the strength setting unit 101 sets the strength of the median filter processing to be stronger as the body thickness BT is thicker.

In FIG. 19, in a strength table 103G for Gaussian filter processing, the size of the Gaussian filter 110 to the body thickness BT is registered. In the size of the Gaussian filter 110, a greater size is registered as the body thickness BT is thicker. Specifically, in a case where the body thickness BT is less than 10 cm, 3×3 is registered, in a case where the body thickness BT is equal to or greater than 10 cm and less than 15 cm, 5×5 is registered, in a case where the body thickness BT is equal to or greater than 15 cm and less than 20 cm, 7×7 is registered, . . . The Gaussian filter 110 of 3×3 is as shown in FIG. 16. The Gaussian filter 110 of 5×5 has 25 coefficients of a denominator X=256 decided based on the Gaussian distribution. The Gaussian filter 110 of 7×7 has 49 coefficients of a denominator X=4096 decided based on the Gaussian distribution. That is, in a case of the Gaussian filter 110, the size is changed to change the coefficients. In this way, similarly to the strength table 103 for recursive filter processing and the strength table 103 for median filter processing, the strength table 103G for Gaussian filter processing also has the content that the thicker the body thickness BT, the stronger the strength of the Gaussian filter processing. Accordingly, the strength setting unit 101 sets the strength of the Gaussian filter processing to be stronger as the body thickness BT is thicker.

Figure 20:
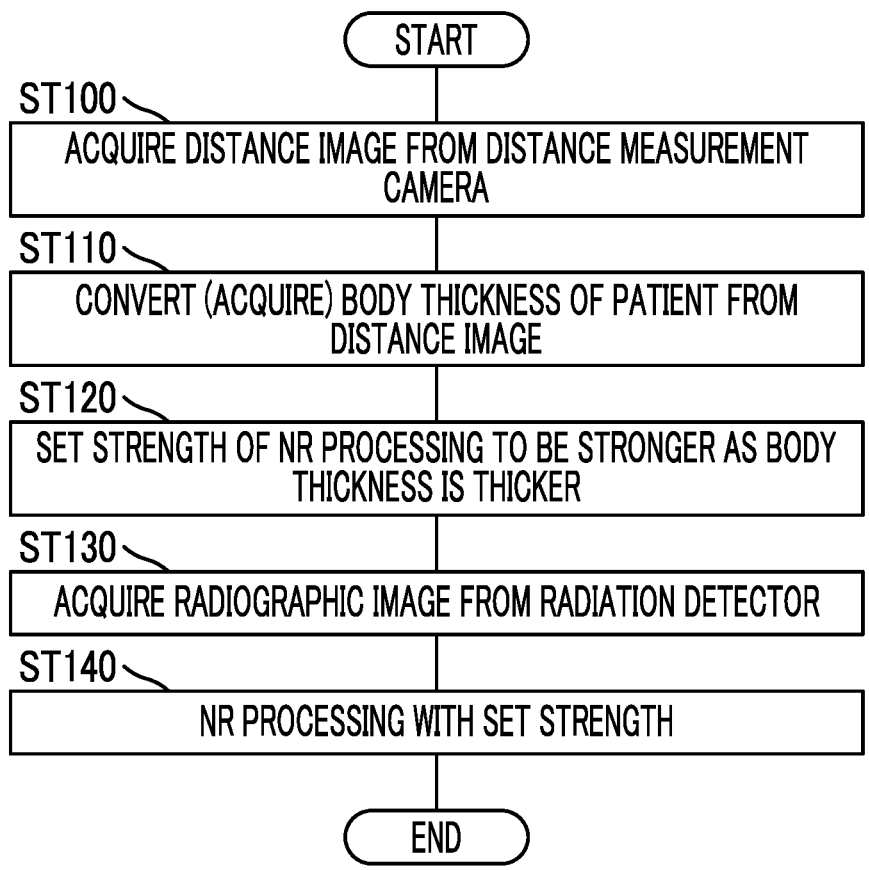
FIG. 20 is a flowchart showing a processing procedure of a processing apparatus.

Next, the operation of the above-described configuration will be described referring to a flowchart of FIG. 20. In a case where the first operation program 75 is activated, as shown in FIG. 12, the CPU 67 of the console 11 functions as the radiation source controller 80, the collimator controller 81, the distance measurement camera controller 82, the distance image acquisition unit 83, the detector controller 84, the radiographic image acquisition unit 85, the imaging instruction reception unit 86, and the display controller 87. In a case where the second operation program 76 is activated, as shown in FIG. 12, the FPGA 68 of the console 11 functions as the image processing unit 90.

As shown in FIG. 8, prior to radioscopy, the imaging menu corresponding to the imaging order is selected by the operator OP, and accordingly, the irradiation conditions are set in the voltage generator 41 by the radiation source controller 80. The adjustment of the opening degree of the emission opening of the collimator 31 is performed by the collimator controller 81. Subsequently, positioning of the radiation source 30, the radiation detector 33, and the patient P is performed by the operator OP. Thereafter, the foot switch 22 is depressed by the operator OP, and radioscopy is started.

Before radioscopy is started, as shown in FIG. 9, under the control of the distance measurement camera controller 82, the imaging operation of the distance image 55 is performed by the distance measurement camera 32 in synchronization with the timing at which the radiation detector 33 outputs the offset correction image 45O. The distance image 55 is transmitted from the distance measurement camera 32 to the console 11 and is acquired with the distance image acquisition unit 83 (Step ST100).

As shown in FIG. 13, the distance image 55 is output from the distance image acquisition unit 83 to the body thickness conversion unit 100 of the image processing unit 90. In the body thickness conversion unit 100, the body thickness BT is converted from the distance image 55 as shown in FIG. 7 (Step ST110). With this, the body thickness BT is acquired. The body thickness BT is output from the body thickness conversion unit 100 to the strength setting unit 101. Step ST110 is an example of "body thickness acquisition processing" according to the technique of the present disclosure.

As shown in FIGS. 13 and 17 to 19, the strength setting unit 101 sets the strength of the NR processing to be stronger as the body thickness BT is thicker (Step ST120). A setting result of the strength is output from the strength setting unit 101 to the NR processing unit 102. Step ST120 is an example of "strength setting processing" according to the technique of the present disclosure.

In a case where radioscopy is started, as shown in FIG. 9, the irradiation of the radiation R from the radiation source 30 is performed in a pulsed manner under the control of the radiation source controller 80. The detection operation is repeated by the radiation detector 33 in synchronization with the irradiation of the radiation R under the control of the detector controller 84. With this, the radiographic image 45 is output from the radiation detector 33. The radiographic image 45 is transmitted from the radiation detector 33 to the console 11 and is acquired with the radiographic image acquisition unit 85 (Step ST130). Step ST130 is an example of "image acquisition processing" according to the technique of the present disclosure.

The radiographic image 45 is output from the radiographic image acquisition unit 85 to the image processing unit 90. Then, in the image processing unit 90, the offset correction processing and the like using the offset correction image 45O is executed to the radiographic image 45. By the NR processing unit 102, the NR processing, such as the recursive filter processing shown in FIG. 14 or the spatial filter processing shown FIGS. 15 and 16, is executed to the radiographic image 45 with the strength set with the strength setting unit 101 (Step ST140). The radiographic image 45 subjected to the NR processing and the like is output from the image processing unit 90 to the display controller 87. Then, the radiographic image 45 is displayed on the operator monitor 21 and is provided for observation of the operator OP under the control of the display controller 87. Step ST140 is an example of "image processing" according to the technique of the present disclosure.

As described above, the CPU 67 of the console 11 functions as the radiographic image acquisition unit 85. The FPGA 68 of the console 11 functions as the image processing unit 90. The image processing unit 90 has a body thickness conversion unit 100, the strength setting unit 101, and the NR processing unit 102. The body thickness conversion unit 100 converts the body thickness BT from the distance image 55 imaged by the distance measurement camera 32 to acquire the body thickness BT. The strength setting unit 101 sets the strength of the NR processing to the radiographic image 45 to be stronger as the body thickness BT is thicker. The radiographic image acquisition unit 85 acquires the radiographic image 45 output from the radiation detector 33 in radioscopy. The NR processing unit 102 executes the NR processing on the radiographic image 45 with the strength set by the strength setting unit 101.

In a case where the body thickness BT is thick, the dose of the radiation R that reaches the radiation detector 33 is extremely smaller, and noise of the radiographic image 45 is more conspicuous. For this reason, the strength of the NR processing needs to be stronger as the body thickness BT is thicker. In the technique of the present disclosure, the strength of the NR processing is set to be stronger as the body thickness BT is duly thicker. Accordingly, it is possible to execute appropriate NR processing corresponding to the body thickness BT.

The NR processing unit 102 executes, as the NR processing, the recursive filter processing of adding the past image 45B output further in the past than the processing target image 45A to the processing target image 45A. The strength setting unit 101 sets the number of past images 45B added to the processing target image 45A and the weighting coefficients K to the past images 45B to set the strength. Accordingly, it is possible to execute appropriate recursive filter processing corresponding to the body thickness BT.

The NR processing unit 102 executes, the NR processing, the spatial filter processing, such as the median filter processing using the median filter or the Gaussian filter processing using the Gaussian filter 110. The strength setting unit 101 sets the size of the median filter and the coefficient of the Gaussian filter 110 to set the strength. Accordingly, it is possible to execute appropriate spatial filter processing corresponding to the body thickness BT.

The distance measurement camera controller 82 makes the distance measurement camera 32 measure the body thickness BT of the patient P in a case where the irradiation of the radiation R is not performed. In radioscopy, for example, there is a case where the irradiation of the radiation R is stopped once and the posture of the patient P is changed several times, such as orthopedic reduction. For example, in a case where the irradiation of the radiation R is not performed, and in a case where the distance measurement camera 32 is made to measure the body thickness BT of the patient P, even though the posture of the patient P is changed while the irradiation of the radiation R is stopped once, it is possible to obtain the body thickness BT corresponding to the changed posture.

The distance measurement camera controller 82 makes the distance measurement camera 32 measure the body thickness BT of the patient P in synchronization with the timing at which the radiation detector 33 outputs the offset correction image 45O. The timing at which the radiation detector 33 outputs the offset correction image 45O is inevitably a timing at which the irradiation of the radiation R is not performed. The detection interval DI at which the radiation detector 33 outputs the offset correction image 45O is comparatively frequent. For this reason, in a case where the distance measurement camera 32 is made to measure the body thickness BT of the patient P in synchronization with the timing at which the radiation detector 33 outputs the offset correction image 45O, it is possible to reliably measure the body thickness BT before radioscopy.

As a "body thickness measurement sensor" according to the technique of the present disclosure, the distance measurement camera 32 that is attached to the radiation source 30 and measures the distance between the radiation source 30 and the body surface of the patient P using the TOF system is used. As the body thickness measurement sensor, a stereo camera that measures a distance to an object from an image imaged with two cameras having parallax may be used, instead of the illustrated distance measurement camera 32. Alternatively, an ultrasound sensor that emits an ultrasonic wave from an ultrasound transducer to measure a distance to an object based on an ultrasound echo reflected from the object may be used. The distance measurement camera 32 is more preferable because the distance between the radiation source 30 and the body surface of the patient P can be more accurately measured and a simple device configuration can be made, compared to the stereo camera, the ultrasound sensor, or the like.

In FIG. 17, although an example where both the number of added images and the weighting coefficient K are changed depending on the body thickness BT has been described, the present disclosure is not limited thereto. At least one of the number of added images or the weighting coefficient K may be changed.

The timing at which the distance measurement camera 32 is made to measure the body thickness BT is not limited to the exemplified timing at which the radiation detector 33 outputs the offset correction image 45O. The distance measurement camera 32 may be made to measure the body thickness BT at regular intervals simply while the depression of the foot switch 22 is released.

Second Embodiment

Figure 21:
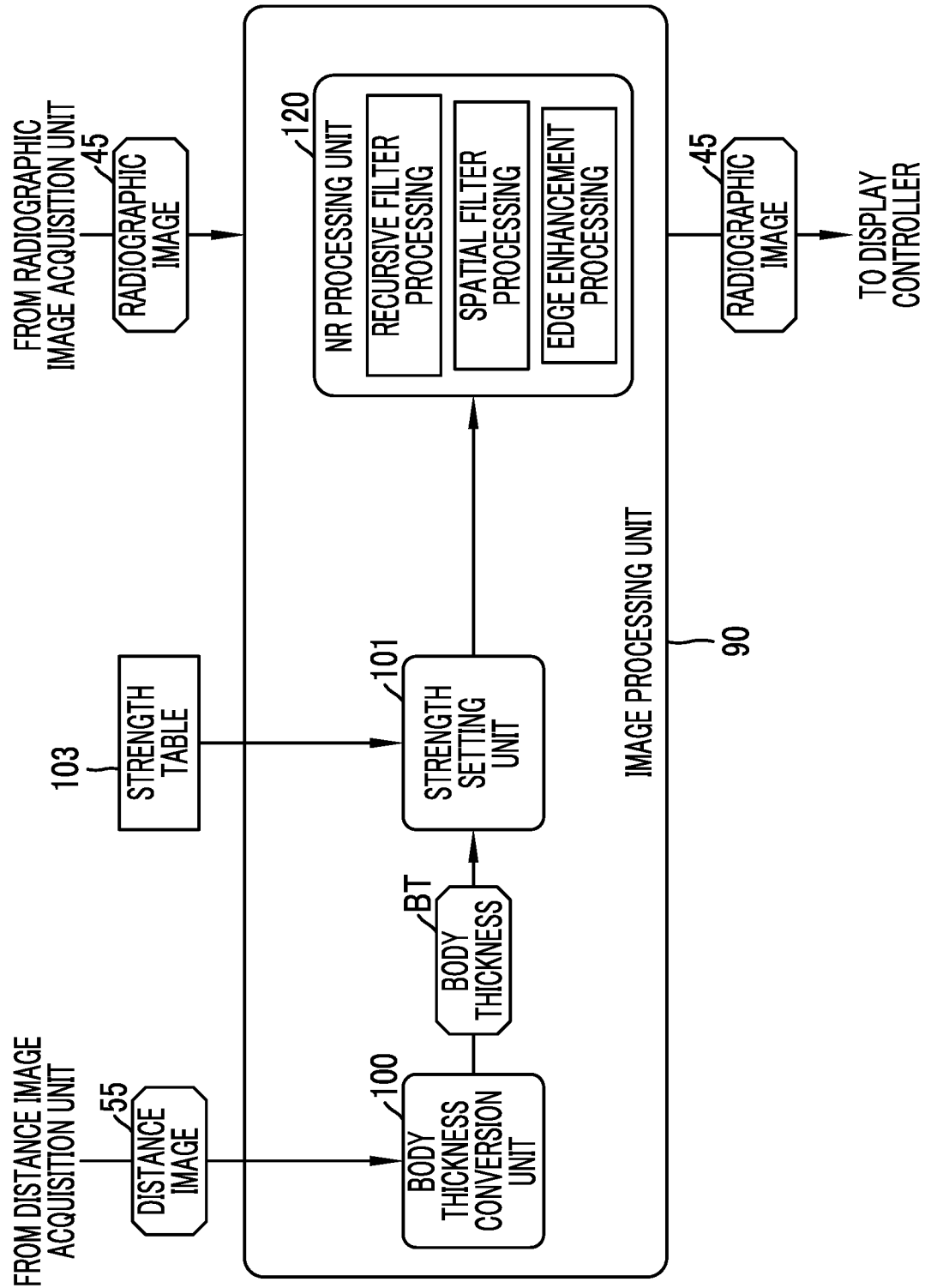
FIG. 21 is a block diagram showing an NR processing unit of a second embodiment.

In FIG. 21, a NR processing unit 120 of a second embodiment executes edge enhancement processing on the radiographic image 45, in addition to the recursive filter processing and the spatial filter processing described above. The edge enhancement processing is processing of enhancing an edge of a structure (hereinafter, referred to as a low spatial frequency structure) in which a spatial frequency is relatively low in the radiographic image 45.

A structure (hereinafter, referred to as a high spatial frequency structure) in which the spatial frequency is relatively high in the radiographic image 45 is highly likely to be noise. In contrast, the low spatial frequency structure is highly likely to be an observation target, such as a bone or an organ of the patient P. Note that the spatial filter processing smooths not only the edge of the high spatial frequency structure highly likely to be noise, but also the edge of the low spatial frequency structure highly likely to be an observation target. Therefore, in the second embodiment, the edge of the low spatial frequency structure smoothed with the spatial filter processing and hardly observed is easily observed through the edge enhancement processing. For this reason, according to the second embodiment, it is possible to provide the operator OP with the radiographic image 45 in which an observation target is clearer.

Similarly to the NR processing, the strength of the edge enhancement processing may be set to be stronger as the body thickness BT is thicker. For example, as shown in a table 125A of FIG. 22A, setting is made such that the edge enhancement processing is not executed in a case where the body thickness BT is less than 15 cm, and the edge enhancement processing is executed in a case where the body thickness BT is equal to or greater than 15 cm. Alternatively, as shown in a table 125B of FIG. 22B, setting may be made such that the level of the strength of the edge enhancement processing is made to be higher as the body thickness BT is stronger.

The strength of the NR processing is set to be stronger as the body thickness BT is thicker, and thus, a degree of smoothing of the edge of the low spatial frequency structure through the spatial filter processing is also higher as the body thickness BT is thicker. Accordingly, in a case where the strength of the edge enhancement processing is set to be stronger as the body thickness BT is thicker, it is possible to execute appropriate edge enhancement processing corresponding to the body thickness BT.

Third Embodiment

Figure 23:
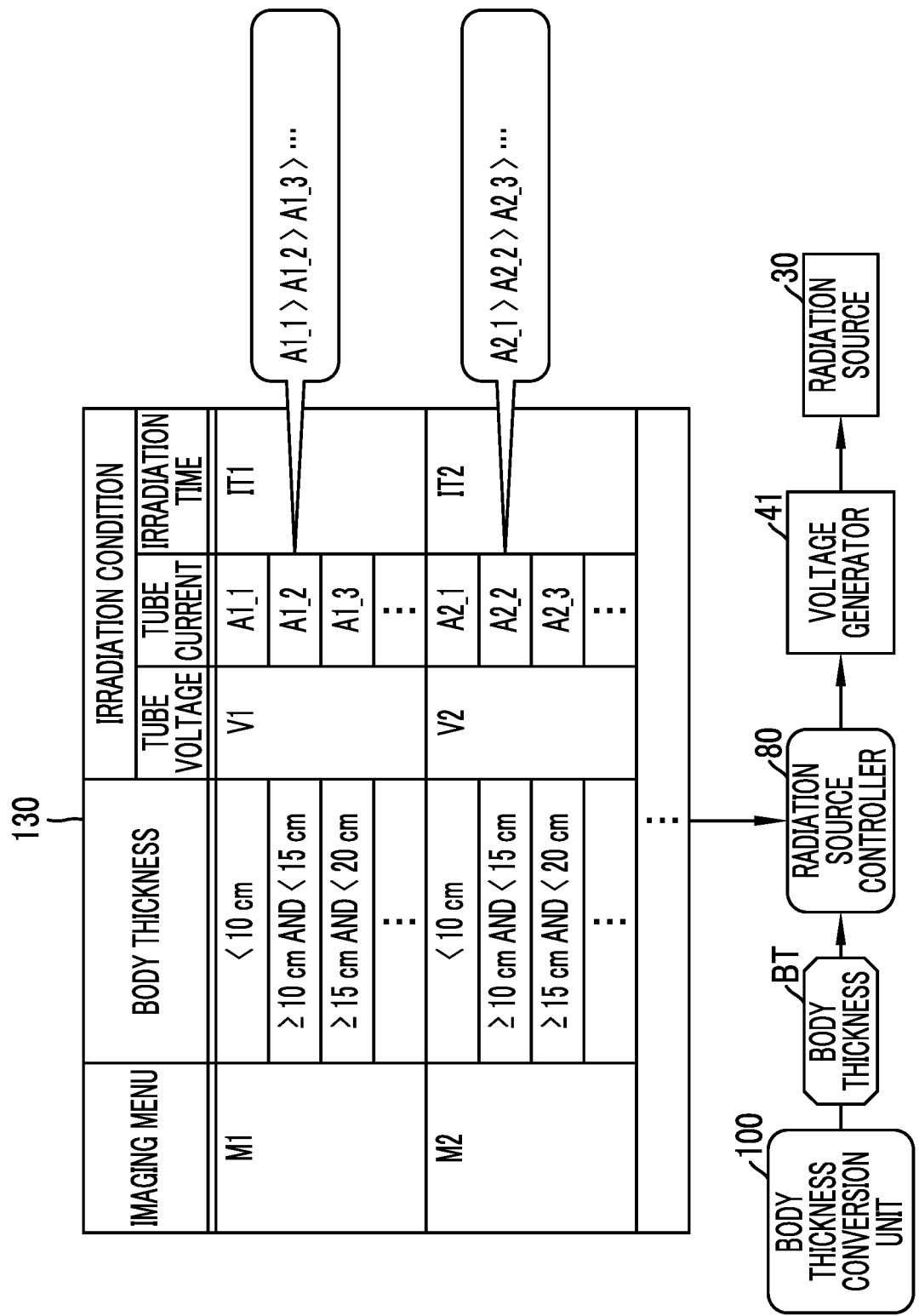
FIG. 23 is a diagram showing a third embodiment where a tube current is set to be lower as the body thickness is thicker, and the radiation source performs irradiation of radiation with the set tube current.

In a third embodiment shown in FIG. 23, an irradiation condition table 130 is used, instead of the irradiation condition table 60 shown in FIG. 8.

The irradiation condition table 130 is different from the irradiation condition table 60 in that, in an imaging menu, a plurality of tube currents are set depending on to the body thickness BT. The tube current is set to a lower value as the body thickness BT is thicker. For example, In a tube current of an imaging menu Ml, in a case where the body thickness BT is less than 10 cm, A1_1 is registered, in a case where the body thickness BT is equal to or greater than 10 cm and less than 15 cm, A1_2 is registered, in a case where the body thickness BT is equal to or greater than 15 cm and less than 20 cm, A1_3 is registered, . . . Then, A1_1>A1_2> A1_3> . . . For example, A1_1=50 mA, A1_2=45 mA, and A1_3=40 mA.

The radiation source controller 80 sets the irradiation conditions corresponding to the imaging menu instructed through the input device 13 and the body thickness BT from the body thickness conversion unit 100 in the voltage generator 41 with reference to the irradiation condition table 130. The radiation source controller 80 causes the irradiation of the radiation R from the radiation source 30 through the voltage generator 41 under the set irradiation conditions.

As in the example, in a case where the distance between the radiation source 30 and the surface of the imaging table 20 is invariable, the thicker of the body thickness BT, the shorter the distance between the radiation source 30 and the body surface of the patient P. For this reason, in a case where the body thickness BT is thickened, a skin dose of the patient P inevitably increases. Note that, in the third embodiment, the radiation source controller 80 sets the tube current to be lower as the body thickness BT is thicker, and makes the radiation source 30 perform the irradiation of the radiation R with the set tube current. For this reason, it is possible to avoid an increase in skin dose to the patient P of which the body thickness BT is comparatively thick.

In a case where the tube current is set to be low, the dose of the radiation R decreases. For this reason, noise of the radiographic image 45 is more conspicuous. Note that, in the technique of the present disclosure, the thicker the body thickness BT, the stronger the strength of the NR processing. Accordingly, it is possible to obtain the radiographic image 45 in which noise is effectively removed, while avoiding an increase in skin dose of the patient P.

The third embodiment may be embodied alone as described in Supplementary Items 1 to 3 described below. That is, instead of setting the strength of the NR processing to be stronger as the body thickness BT and executing the NR processing on the radiographic image 45 with the set strength, the tube current may be set to be lower as the body thickness BT is thicker, and the radiation source 30 may be made to perform the irradiation of the radiation R with the set tube current. "Tube current setting processing" and "radiation source control processing" described in Supplementary Items 2 and 3 are charged by the radiation source controller 80.

Supplementary Item 1

A processing apparatus that is used for a radioscopy apparatus including a radiation source configured to continuously irradiate a subject with radiation and a radiation detector configured to detect the radiation transmitted through the subject to output a radiographic image, the processing apparatus comprising:
  at least one processor,
  in which the processor is configured to
    acquire a body thickness of the subject measured by a body thickness measurement sensor,
    set a tube current for performing the irradiation of the radiation to be lower as the body thickness is thicker, and
    make the radiation source perform the irradiation of the radiation with the set tube current.

Supplementary Item 2

A method of operating a processing apparatus that is used for a radioscopy apparatus including a radiation source configured to continuously irradiate a subject with radiation and a radiation detector configured to detect the radiation transmitted through the subject to output a radiographic image,
  in which a processor executes:
    body thickness acquisition processing of acquiring a body thickness of the subject measured by a body thickness measurement sensor;
    tube current setting processing of setting a tube current for irradiation of the radiation to be lower as the body thickness is thicker; and
    radiation source control processing of make the radiation source perform the irradiation of the radiation with the set tube current.

Supplementary Item 3

An operation program for a processing apparatus that is used for a radioscopy apparatus including a radiation source configured to continuously irradiate a subject with radiation and a radiation detector configured to detect the radiation transmitted through the subject to output a radiographic image, the operation program causing a processor to execute:
  body thickness acquisition processing of acquiring a body thickness of the subject measured by a body thickness measurement sensor;
  tube current setting processing of setting a tube current for irradiation of the radiation to be lower as the body thickness is thicker; and
  radiation source control processing of making the radiation source perform the irradiation of the radiation with the set tube current.

Fourth Embodiment

Figure 24:
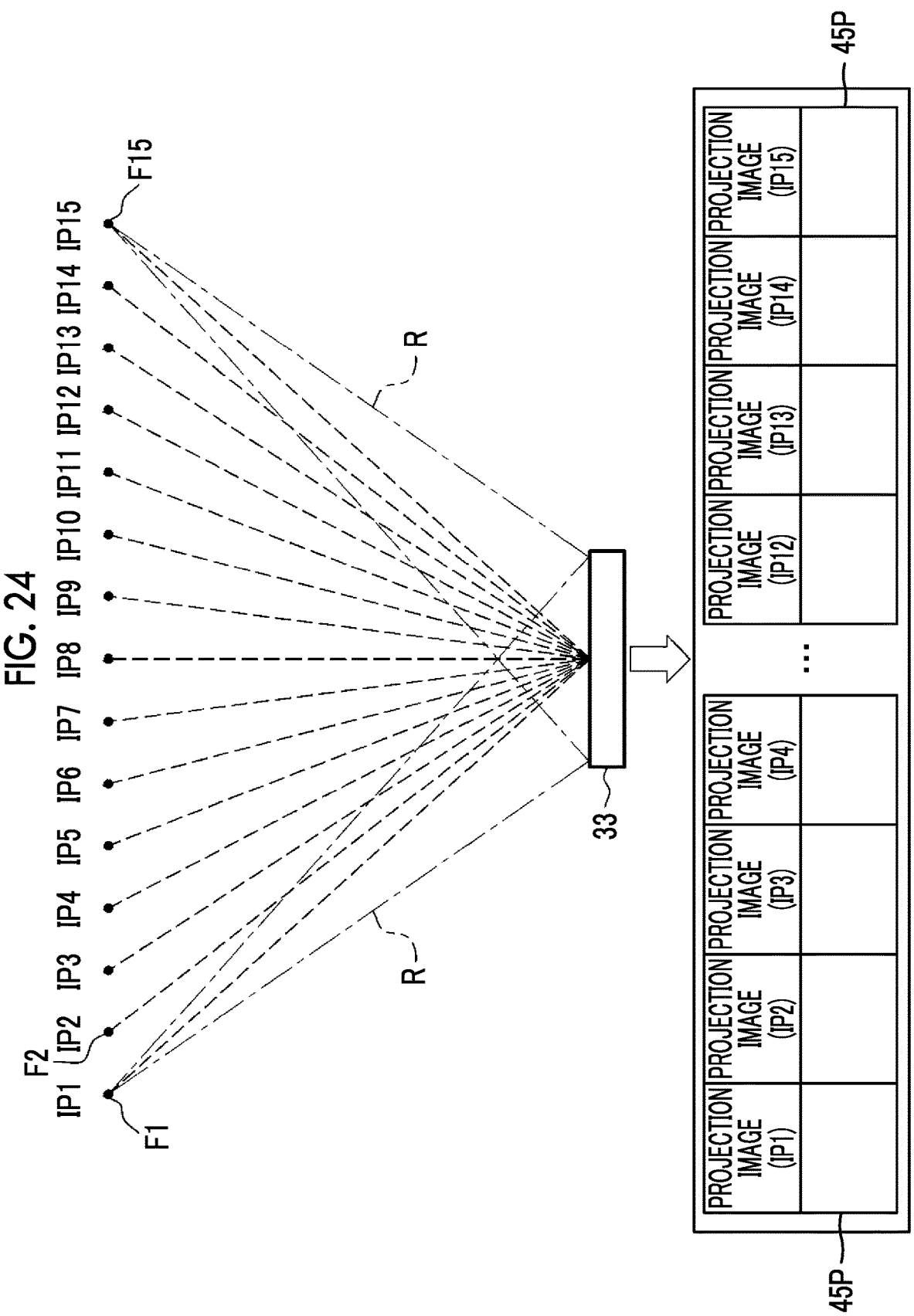
FIG. 24 is a diagram showing a manner of tomosynthesis imaging.
Figure 25:
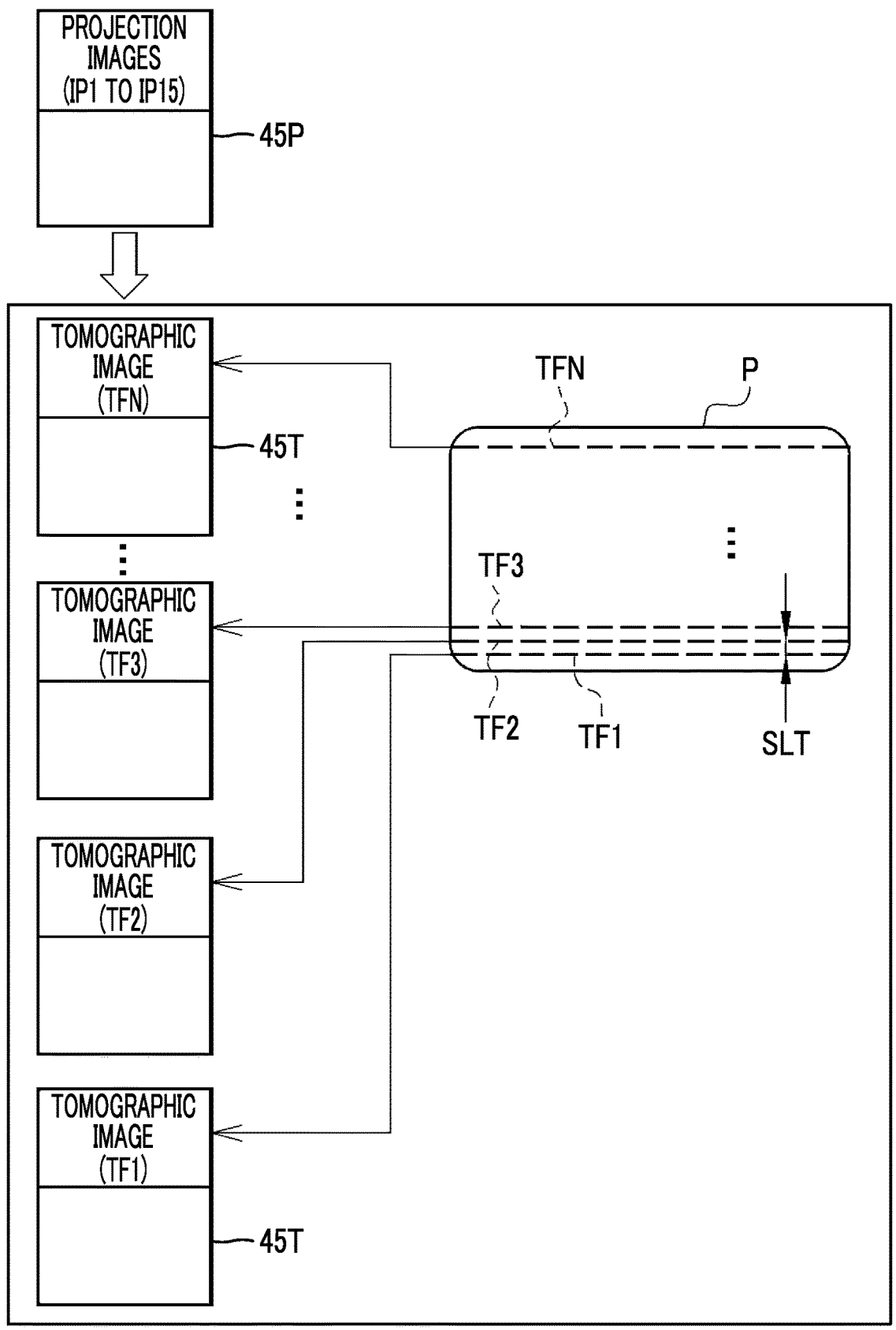
FIG. 25 is a diagram showing a manner of reconfiguring tomographic images from a plurality of projection images obtained by tomosynthesis imaging.
Figure 26:
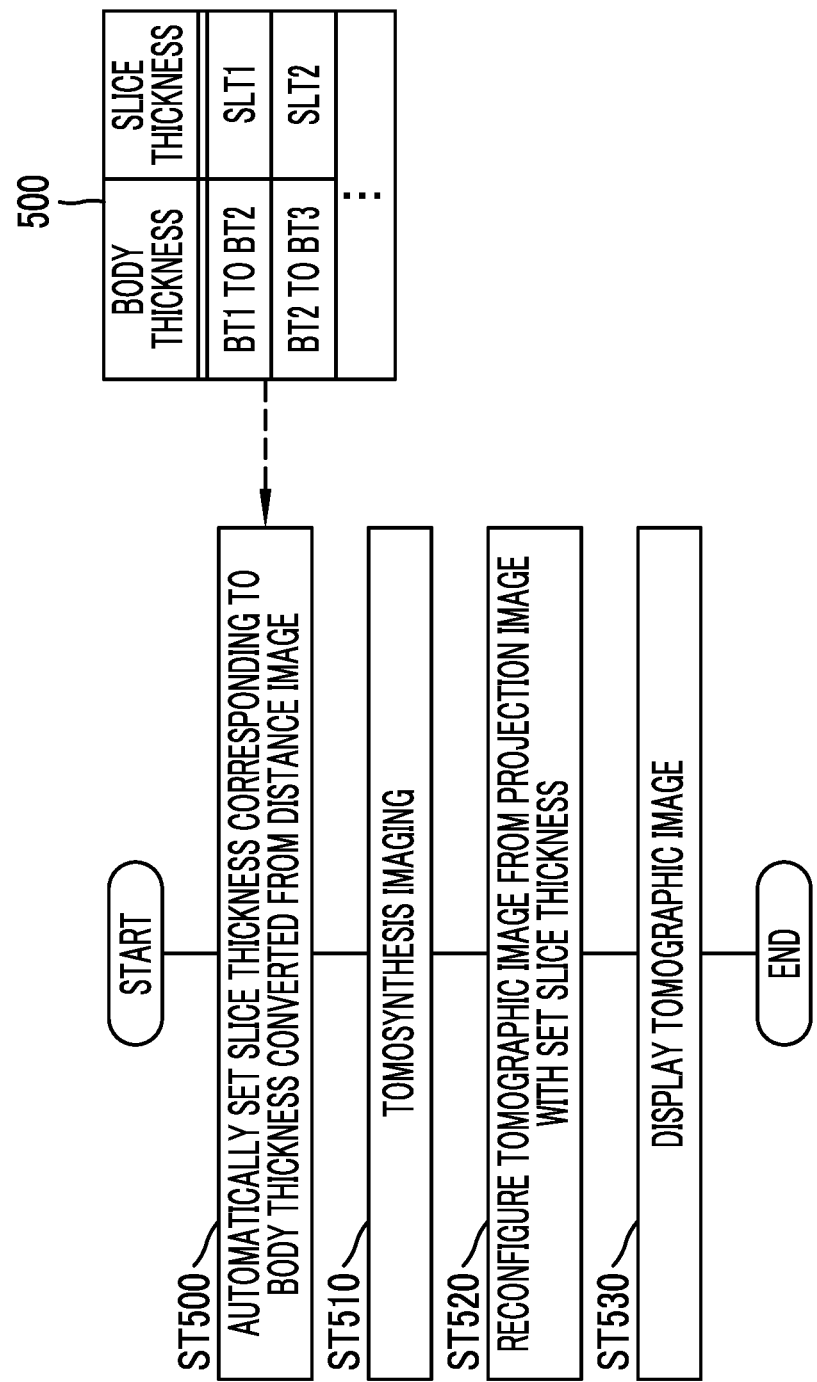
FIG. 26 is a flowchart showing a procedure of a fourth embodiment.

In a fourth embodiment shown in FIGS. 24 to 26, tomosynthesis imaging is performed in addition to radioscopy.

As shown in FIG. 24, tomosynthesis imaging is imaging where the radiation source 30 is sequentially moved to a plurality of irradiation positions IP arranged at equal intervals along the longitudinal direction of the imaging table 20, the irradiation of the radiation R is performed from a plurality of focuses F corresponding to the respective irradiation positions IP to the radiation detector 33, and the radiographic image 45 (hereinafter, referred to as a projection image 45P) is output from the radiation detector 33 each time. In tomosynthesis imaging, the radiation detector 33 is placed at the center of the irradiation position IP. FIG. 24 shows an example of tomosynthesis imaging where the irradiation of the radiation R is performed from 15 focuses F1 to F15 corresponding to 15 irradiation positions IP1 to IP15 centering on an irradiation position IP8, and 15 projection images 45P are obtained.

As shown in FIG. 25, the image processing unit 90 reconfigures tomographic images 45T corresponding to tomographic planes TF1 to TFN of the patient P from the projection images 45P obtained through tomosynthesis imaging shown in FIG. 24 using a known method, such as a filtered back projection method. The image processing unit 90 reconfigures the tomographic image 45T with a slice thickness SLT set in advance. The display controller 87 displays the tomographic images 45T on the operator monitor 21.

As shown in FIG. 26, in the console 11, the slice thickness SLT corresponding to the body thickness BT of the patient P converted from the distance image 55 is automatically set with reference to a slice thickness table 500 (Step ST500). In the slice thickness table 500, the slice thickness SLT of a greater value is registered as the body thickness is thicker. The slice thickness table 500 is stored in the storage device 65.

After the slice thickness SLT is automatically set, tomosynthesis imaging shown in FIG. 24 is performed (Step ST510). With this, a plurality of projection image 45P corresponding to the respective irradiation positions IP are obtained. Then, as shown in FIG. 25, the tomographic image 45T is reconfigured from the projection image 45P with the automatically set slice thickness SLT by the image processing unit 90 (Step ST520). The reconfigured tomographic image 45T is displayed on the operator monitor 21 under the control of the display controller 87 (Step ST530).

Figure 27:
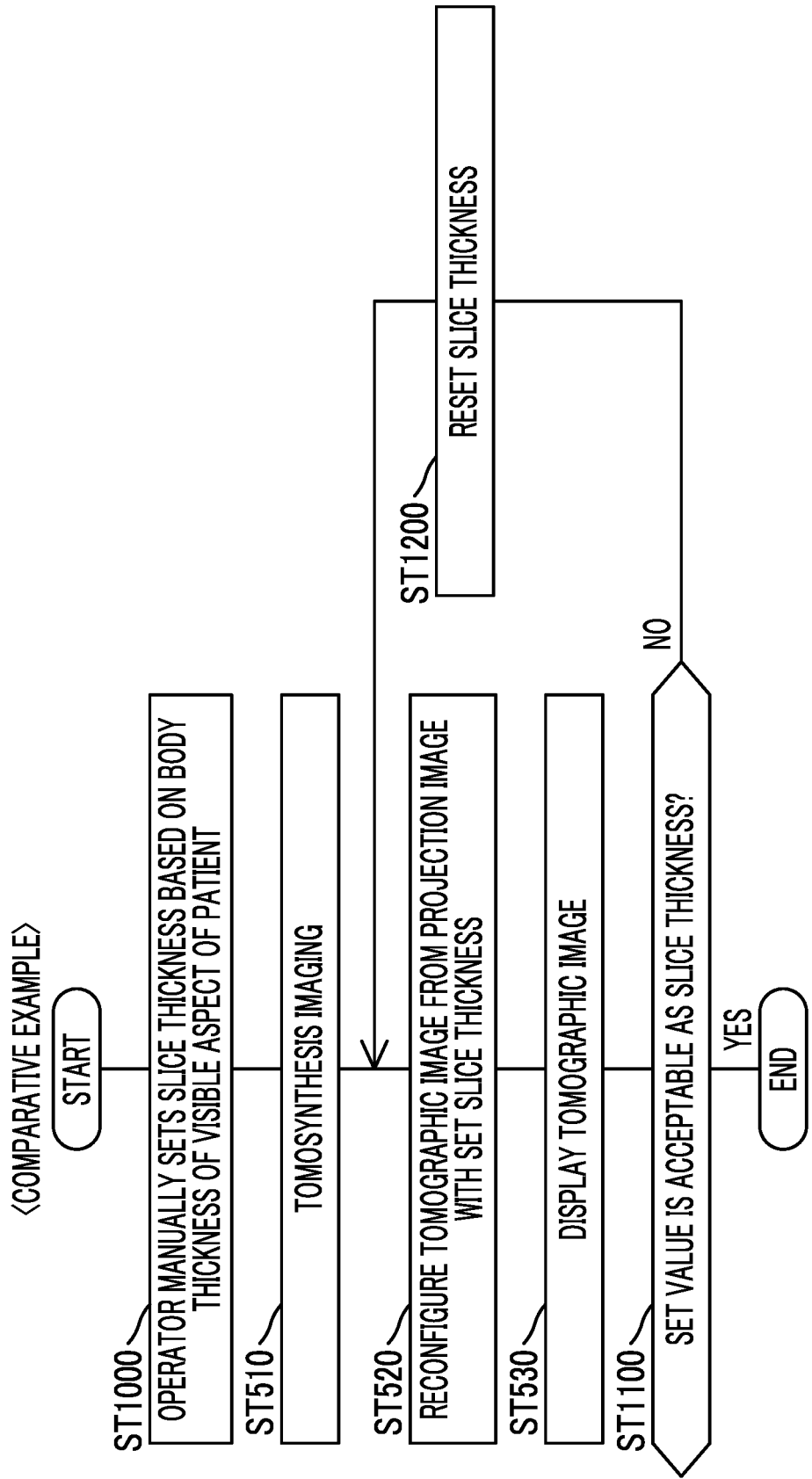
FIG. 27 is a flowchart showing a procedure in the related art as a comparative example.

FIG. 27 is a flowchart showing a procedure in the related art as a comparative example. In the related art, the operator OP manually sets a slice thickness SLT through the input device 13 based on a body thickness BT of a visible aspect of the patient P (Step ST1000). For this reason, the operator OP determines whether or not a set value is acceptable as the slice thickness SLT by the tomographic image 45T displayed on the operator monitor 21 (Step ST1100). Then, in a case where the set value is not acceptable as the slice thickness SLT (in Step ST1100, NO), the operator OP resets the slice thickness SLT (Step ST1200), and the processing of Steps ST520 and ST530 is repeated. A time of about several minutes is needed in reconfiguring the tomographic image 45T from the projection image 45P after the slice thickness SLT is reset. Therefore, in the related art, there is a case where a time is needed to obtain a tomographic image 45T at a desired slice thickness SLT.

In the fourth embodiment, as shown in FIG. 26, the slice thickness SLT is automatically set depending on the body thickness BT of the patient P converted from the distance image 55. Accordingly, a lot of labor is not needed to manually set the slice thickness SLT unlike the related art, and a lot of time is not needed until the tomographic image 45T of a desired slice thickness SLT is obtained.

Although the distance between the radiation source 30 and the surface of the imaging table 20 is invariable, the present disclosure is not limited thereto. A configuration may be made in which the distance between the imaging table 20 and the radiation source 30 is variable.

Although the patient P is exemplified as the subject, the present disclosure is not limited thereto. A pet, such as a dog or a cat, or a domestic animal, such as a horse or cattle, may be a subject.

The hardware configuration of the computer constituting the console 11 can be modified in various ways. The console 11 can also be constituted of a plurality of computers separated as hardware for the purpose of improving processing capability and reliability. For example, the functions of the respective units 80 to 87 constructed in the CPU 67 and the function of the image processing unit 90 constructed in the FPGA 68 are distributed to two computers. In this case, the console 11 is constituted of two computers.

In this way, the hardware configuration of the computer of the console 11 can be appropriately changed depending on required performance, such as processing capability, safety, or reliability. Not only hardware but also an application program, such as the first operation program 75 and the second operation program 76, can be of course duplicated or distributed and stored in a plurality of storage devices for the purpose of ensuring safety and reliability.

As the hardware structures of processing units that execute various kinds of processing, such as the radiation source controller 80, the collimator controller 81, the distance measurement camera controller 82, the distance image acquisition unit 83, the detector controller 84, the radiographic image acquisition unit 85, the imaging instruction reception unit 86, the display controller 87, the image processing unit 90, the body thickness conversion unit 100, the strength setting unit 101, and the NR processing unit 102 or 120, various processors described below can be used. Various processors include at least one of a programmable logic device (PLD) that is a processor capable of changing a circuit configuration after manufacture, such as the FPGA 68, a dedicated electric circuit that is a processor having a circuit configuration dedicatedly designed for executing specific processing, such as an application specific integrated circuit (ASIC), or the like, in addition to the CPU 67 that is a general-purpose processor executing software (first operation program 75) to function as various processing units.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

The technique of the present disclosure can also be appropriately combined with at least one of various embodiments or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A processing apparatus that is used for a radioscopy apparatus including a radiation source configured to continuously irradiate a subject with radiation and a radiation detector configured to detect the radiation transmitted through the subject to output a radiographic image, the processing apparatus comprising:
   at least one processor,
   wherein the processor is configured to;
   acquire a body thickness of the subject measured by a body thickness measurement sensor,
   set a tube current, for performing the irradiation of the radiation, to be lower as the body thickness is thicker,
   set strength of noise reduction processing to the radiographic image to be stronger as the body thickness is thicker,
   cause the radiation source to perform the irradiation of the radiation with the set tube current,
   acquire the radiographic image output from the radiation detector, and
   execute the noise reduction processing on the radiographic image with the set strength.

2. The processing apparatus according to claim 1,
   wherein the processor is configured to execute, as the noise reduction processing, recursive filter processing of adding a past image as the radiographic image output further in the past than a processing target image as the radiographic image to be processed to the processing target image.

3. The processing apparatus according to claim 2,
   wherein the processor is configured to set at least one of the number of past images added to the processing target image or a weighting coefficient to the past image to set the strength.

4. The processing apparatus according to claim 1,
   wherein the processor is configured to execute, as the noise reduction processing, spatial filter processing using a spatial filter.

5. The processing apparatus according to claim 4, wherein the processor is configured to set at least one of a coefficient or a size of the spatial filter to set the strength.

6. The processing apparatus according to claim 4, wherein the processor is configured to execute edge enhancement processing of enhancing an edge of a structure in which a spatial frequency is relatively low in the radiographic image.

7. The processing apparatus according to claim 1, wherein the processor is configured to make the body thickness measurement sensor measure the body thickness in a case where the irradiation of the radiation is not performed.

8. The processing apparatus according to claim 7, wherein the processor is configured to make the body thickness measurement sensor measure the body thickness in synchronization with a timing at which the radiation detector outputs the radiographic image for offset correction.

9. The processing apparatus according to claim 1, wherein the body thickness measurement sensor is a distance measurement camera that outputs a distance image representing a distance to a surface of an object using a time-of-flight system, and the processor is configured to convert the body thickness from the distance image.

10. A method of operating a processing apparatus that is used for a radioscopy apparatus including a radiation source configured to continuously irradiate a subject with radiation and a radiation detector configured to detect the radiation transmitted through the subject to output a radiographic image, the method comprising:
a processor executing:
body thickness acquisition processing of acquiring a body thickness of the subject measured by a body thickness measurement sensor;
tube current setting processing of setting a tube current, for performing the irradiation of the radiation, to be lower as the body thickness is thicker;
strength setting processing of setting strength of noise reduction processing to the radiographic image to be stronger as the body thickness is thicker;
irradiation processing of causing the radiation source to perform the irradiation of the radiation with the set tube current;
image acquisition processing of acquiring the radiographic image output from the radiation detector; and
image processing of executing the noise reduction processing on the radiographic image with the set strength.

11. A non-transitory computer-readable storage medium storing an operation program for a processing apparatus that is used for a radioscopy apparatus including a radiation source configured to continuously irradiate a subject with radiation and a radiation detector configured to detect the radiation transmitted through the subject to output a radiographic image, the operation program being executable by a processor to perform processing comprising:
body thickness acquisition processing of acquiring a body thickness of the subject measured by a body thickness measurement sensor;
tube current setting processing of setting a tube current, for performing the irradiation of the radiation, to be lower as the body thickness is thicker;
strength setting processing of setting strength of noise reduction processing to the radiographic image to be stronger as the body thickness is thicker;
irradiation processing of causing the radiation source to perform the irradiation of the radiation with the set tube current;
image acquisition processing of acquiring the radiographic image output from the radiation detector; and
image processing of executing the noise reduction processing on the radiographic image with the set strength.

12. The processing apparatus according to claim 1, wherein the processor is configured to set the tube current for performing the irradiation of the radiation to be lower as the body thickness is thicker without changing an irradiation time of the radiation.

* * * * *